(12) United States Patent
Hebenstreit et al.

(10) Patent No.: US 9,477,306 B1
(45) Date of Patent: Oct. 25, 2016

(54) MUTAMORPHIC HAPTIC SUBSTRATE

(75) Inventors: Joseph J. Hebenstreit, San Francisco, CA (US); David C. Buuck, Santa Clara, CA (US); Ilya D. Rosenberg, Mountain View, CA (US); Julien G. Beguin, San Francisco, CA (US)

(73) Assignee: Amazon Technologies, Inc., Reno, NV (US)

( * ) Notice: Subject to any disclaimer, the term of this patent is extended or adjusted under 35 U.S.C. 154(b) by 1061 days.

(21) Appl. No.: 12/970,429

(22) Filed: Dec. 16, 2010

Related U.S. Application Data

(60) Provisional application No. 61/376,516, filed on Aug. 24, 2010.

(51) Int. Cl.
 *G06F 3/041* (2006.01)
 *G06F 3/01* (2006.01)
 *G09B 21/00* (2006.01)

(52) U.S. Cl.
 CPC ............. *G06F 3/016* (2013.01); *G09B 21/003* (2013.01)

(58) Field of Classification Search
 CPC ........ G06F 3/016; A61F 9/08; G09B 21/003
 USPC .................................................. 345/172–174
 See application file for complete search history.

(56) References Cited

U.S. PATENT DOCUMENTS

| | | | |
|---|---|---|---|
| 6,781,579 B2 | 8/2004 | Huang et al. | |
| 7,148,882 B2 | 12/2006 | Kamrath et al. | |
| 7,196,694 B2 | 3/2007 | Roberts | |
| 7,973,769 B2* | 7/2011 | Olien | 345/168 |
| 8,269,735 B2 | 9/2012 | Kim et al. | |
| 8,325,159 B2 | 12/2012 | Kent et al. | |
| 2001/0035854 A1 | 11/2001 | Rosenberg et al. | |
| 2003/0162312 A1 | 8/2003 | Takayama et al. | |
| 2005/0017947 A1 | 1/2005 | Shahoian et al. | |
| 2005/0038944 A1 | 2/2005 | Harada et al. | |
| 2005/0107129 A1 | 5/2005 | Kaewell et al. | |
| 2006/0273417 A1 | 12/2006 | Ganapathi et al. | |
| 2007/0097073 A1 | 5/2007 | Takashima et al. | |
| 2007/0257821 A1 | 11/2007 | Son et al. | |
| 2008/0018611 A1 | 1/2008 | Serban et al. | |
| 2008/0094372 A1 | 4/2008 | Philipp | |
| 2008/0185192 A1 | 8/2008 | Hsih | |
| 2008/0287167 A1* | 11/2008 | Caine | G06F 1/1616 455/575.1 |
| 2009/0002328 A1 | 1/2009 | Ullrich et al. | |
| 2009/0225045 A1* | 9/2009 | Liu et al. | 345/173 |

(Continued)

OTHER PUBLICATIONS

Office Action for U.S. Appl. No. 12/970,514, mailed on Oct. 28, 2013, Joseph J. Hebenstreit, "High Resolution Haptic Array," 16 pages.

(Continued)

*Primary Examiner* — Kumar Patel
*Assistant Examiner* — Insa Sadio
(74) *Attorney, Agent, or Firm* — Lee & Hayes, PLLC

(57) ABSTRACT

Substrates for components such as a display, touch sensor, multifunction stackup, and so forth may incorporate one or more haptic actuators configured to generate haptic output. These actuators may be formed from a portion of a body of the substrate, or separate pieces bonded or otherwise affixed to the substrate. Audible output resulting from activation of the actuators may be minimized by coupling the actuators such that they produce a physical displacement of the body of the substrate within, rather than orthogonal to, the plane of the body of the substrate.

31 Claims, 38 Drawing Sheets

(56) References Cited

U.S. PATENT DOCUMENTS

| | | |
|---|---|---|
| 2009/0237374 A1 | 9/2009 | Li et al. |
| 2009/0243817 A1 | 10/2009 | Son |
| 2009/0250267 A1 | 10/2009 | Heubel et al. |
| 2009/0256817 A1 | 10/2009 | Perlin et al. |
| 2009/0273570 A1 | 11/2009 | Degner et al. |
| 2010/0117809 A1 | 5/2010 | Dai et al. |
| 2010/0156814 A1 | 6/2010 | Weber et al. |
| 2010/0156818 A1 | 6/2010 | Burrough et al. |
| 2010/0156841 A1 | 6/2010 | Wang et al. |
| 2010/0156843 A1 | 6/2010 | Paleczny et al. |
| 2010/0160016 A1* | 6/2010 | Shimabukuro ..... G07F 17/3209 463/16 |
| 2010/0265208 A1 | 10/2010 | Kim et al. |
| 2011/0007380 A1 | 1/2011 | Chen |
| 2011/0050591 A1 | 3/2011 | Kim et al. |
| 2011/0063224 A1 | 3/2011 | Vexo et al. |
| 2011/0080347 A1 | 4/2011 | Steeves et al. |
| 2011/0227836 A1 | 9/2011 | Li et al. |
| 2012/0020045 A1 | 1/2012 | Tanase |
| 2012/0026124 A1 | 2/2012 | Li et al. |
| 2012/0139864 A1 | 6/2012 | Sleeman et al. |
| 2012/0162143 A1 | 6/2012 | Kai et al. |
| 2012/0206248 A1 | 8/2012 | Biggs |
| 2013/0044049 A1* | 2/2013 | Biggs et al. .................. 345/156 |
| 2013/0133929 A1* | 5/2013 | Jung .............................. 174/254 |

OTHER PUBLICATIONS

Office action for U.S. Appl. No. 12/970,514, mailed on Jun. 27, 2014, Hebenstreit et al., "High Resolution Haptic Array", 21 pages.
Final Office Action for U.S. Appl. No. 12/970,514, mailed on Jan. 29, 2015, Joseph J. Hebenstreit, "High Resolution Haptic Array", 19 pages.
Office Action for U.S. Appl. No. 12/970,303, mailed on Mar. 26, 2015, Joseph J. Hebenstreit, "Multifunction Stackup", 34 pages.
Office Action for U.S. Appl. No. 12/970,303 mailed on Sep. 15, 2015, Hebenstreit et al., "Multifunction Stackup", 31 pages.
Office action for U.S. Appl. No. 12/970,303, mailed on Mar. 16, 2016, Hebenstreit et al., "Multifunction Stackup", 40 pages.

\* cited by examiner

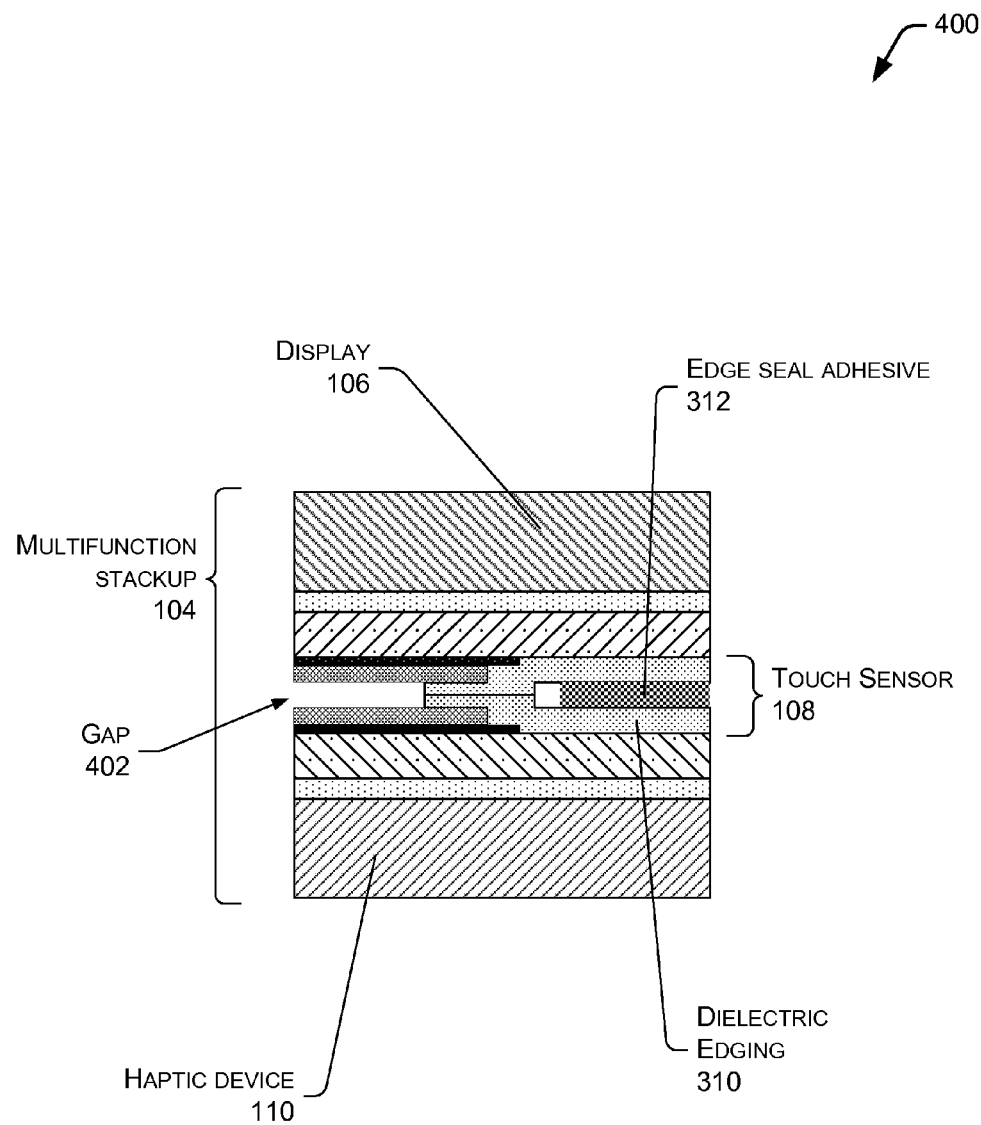
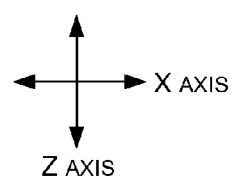
FIG. 4

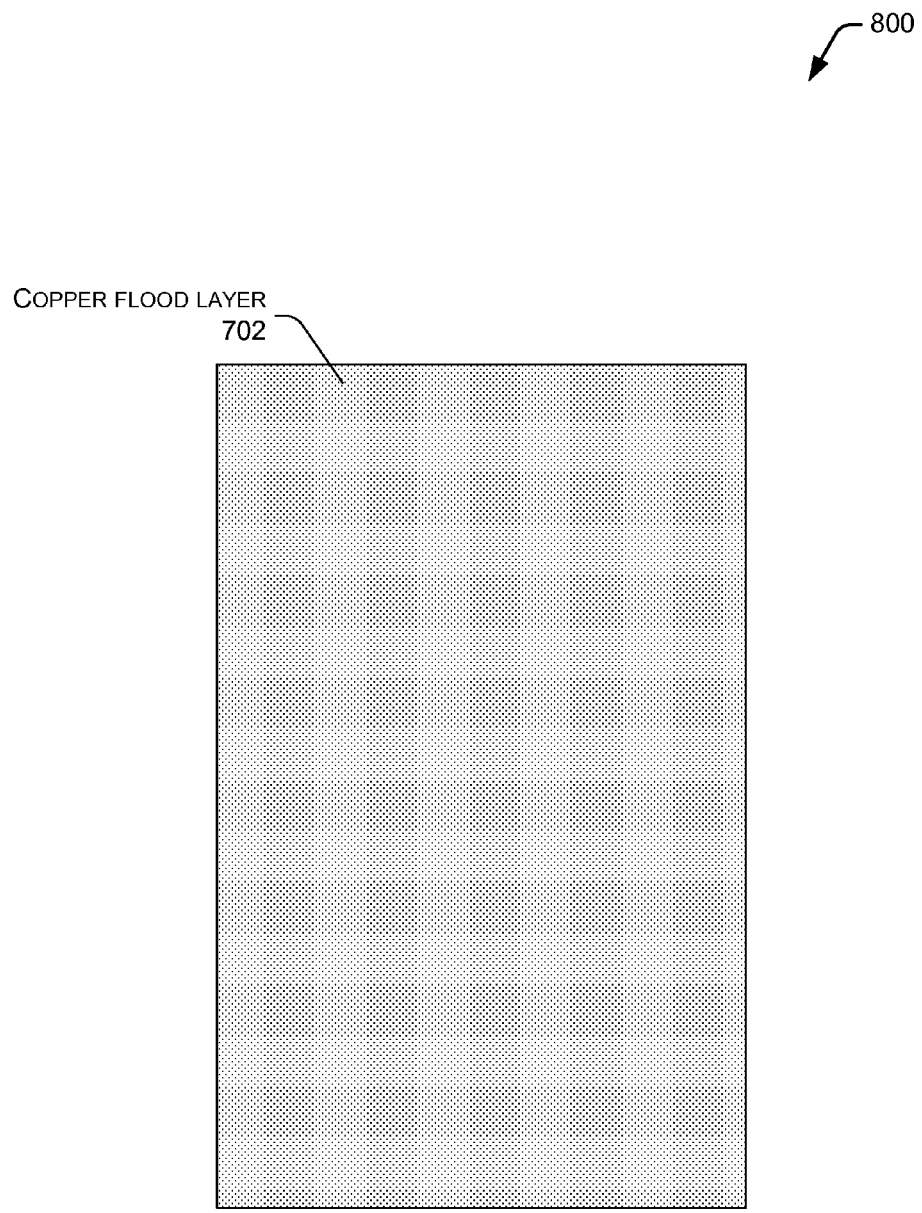
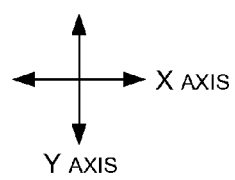
FIG. 8

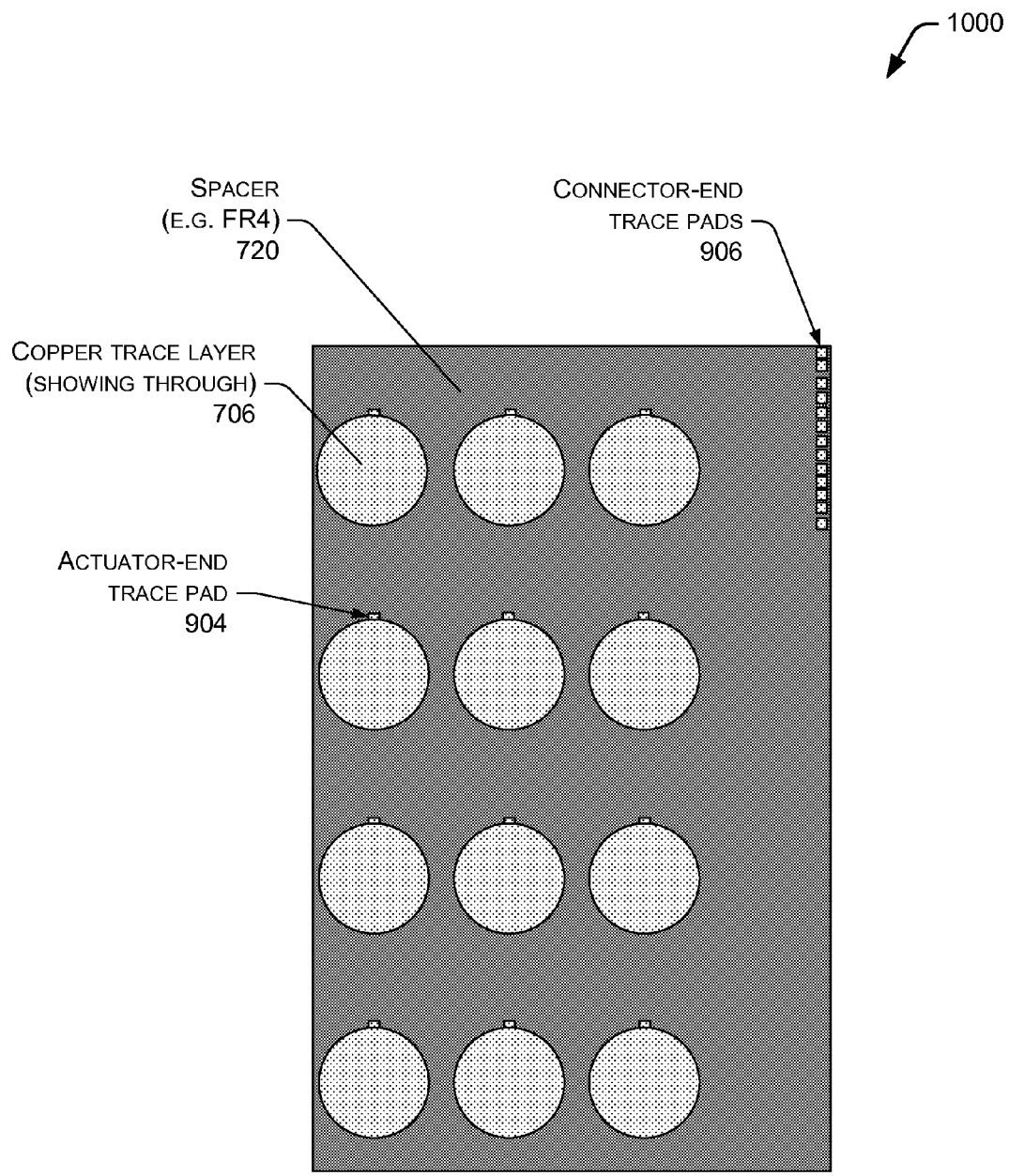
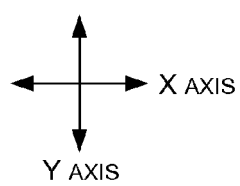
FIG. 10

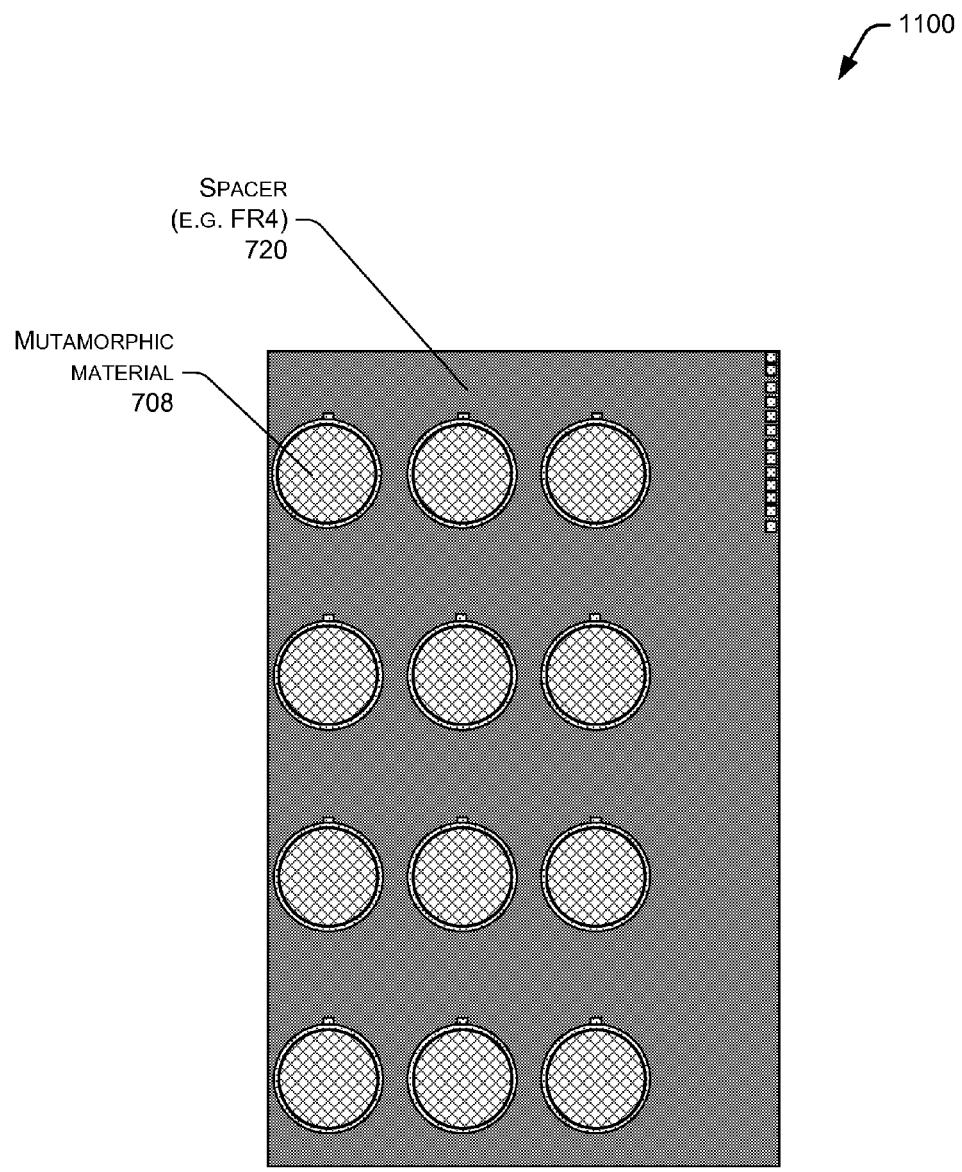
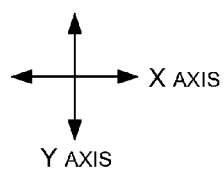
FIG. 11

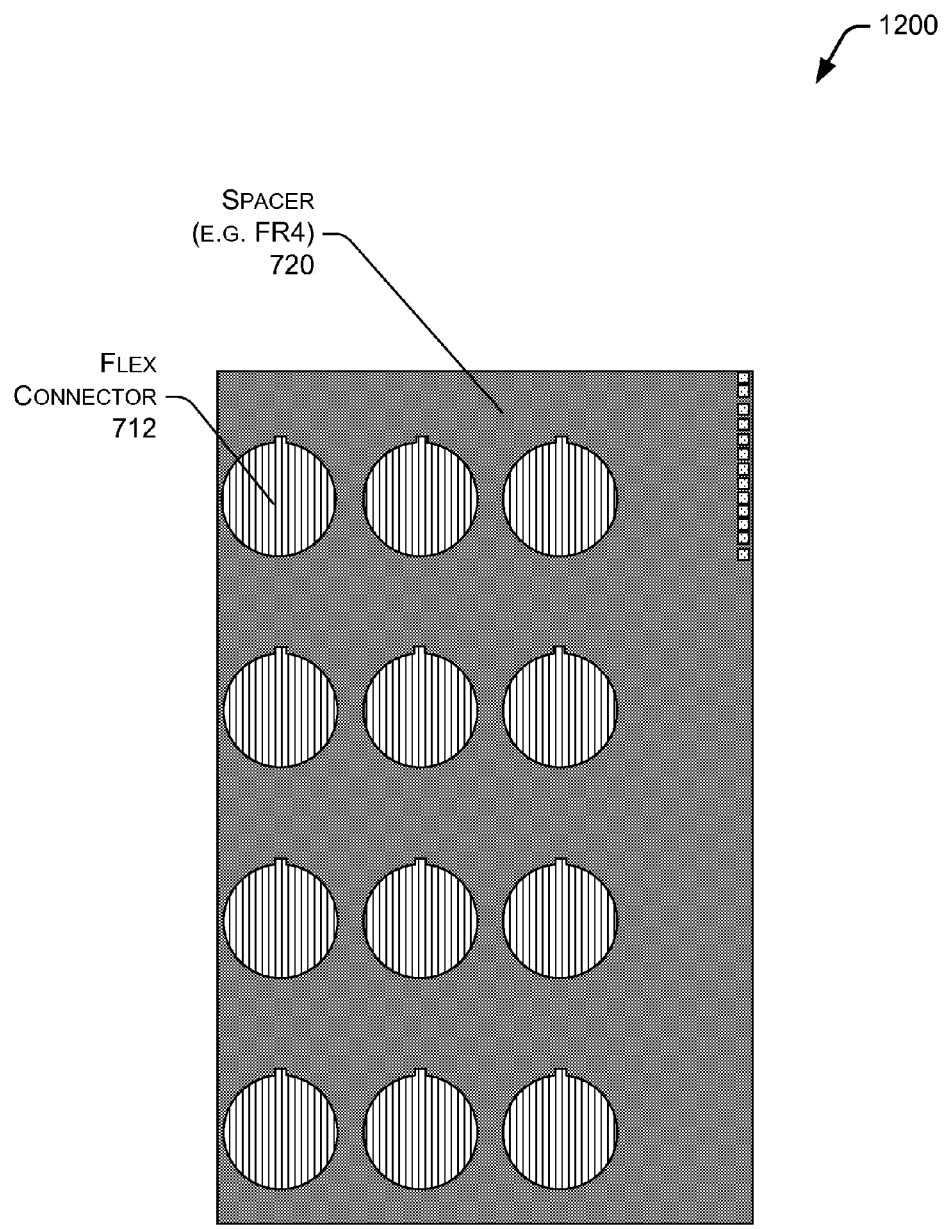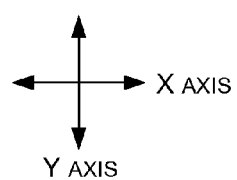
FIG. 12

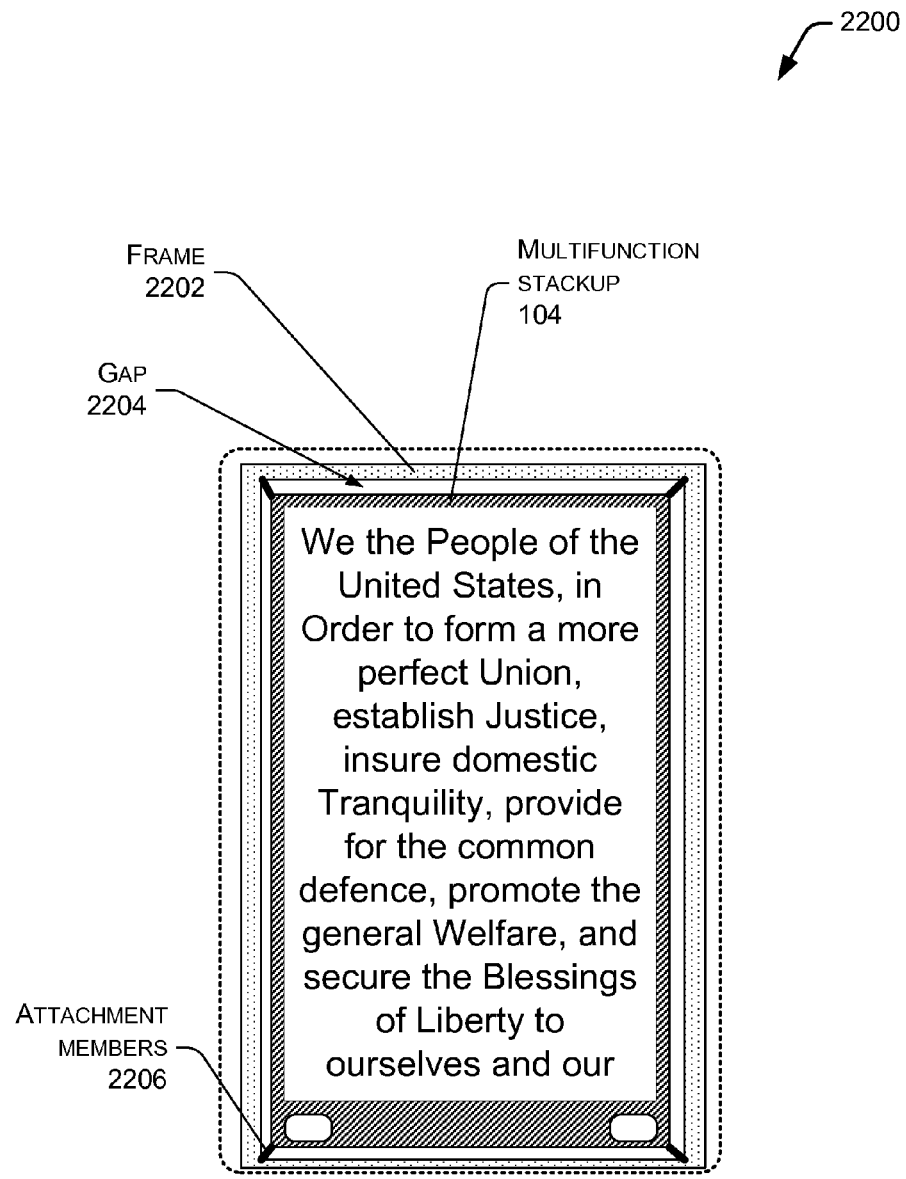
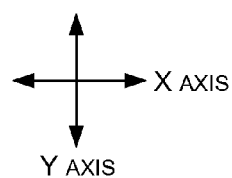
FIG. 22

MUTAMORPHIC HAPTIC SUBSTRATE

PRIORITY

The present application claims priority to U.S. Provisional Application Ser. No. 61/376,516, filed on Aug. 24, 2010, entitled "Multifunction Stackup." This application is herein incorporated by reference in its entirety, and the benefit of the filing date of this application is claimed to the fullest extent permitted.

BACKGROUND

Users increasingly demand devices with multiple capabilities in ever smaller form factors (that is, the overall size of the device). These multiple capabilities may include a touch screen with haptic or tactile feedback. Traditionally, these actuators have been bulky and difficult to implement, particularly in devices with minimal overall heights.

BRIEF DESCRIPTION OF THE DRAWINGS

The detailed description is set forth with reference to the accompanying figures. In the figures, the left-most digit(s) of a reference number identifies the figure in which the reference number first appears. The use of the same reference numbers in different figures indicates similar or identical items.

FIG. 4 illustrates a cross section of the multifunction stackup of FIG. 3 when the two integrated packages are joined via an edge seal adhesive.

FIGS. 8-12 illustrate plan views of the haptic device of FIG. 7 as successive components are affixed.

FIG. 22 is an illustrative plan view of selected portions of the device including a frame to which the multifunction stackup is affixed via a plurality of attachment members under tension to maintain planarity of the multifunction stackup.

DETAILED DESCRIPTION

Overview

Figure 1:
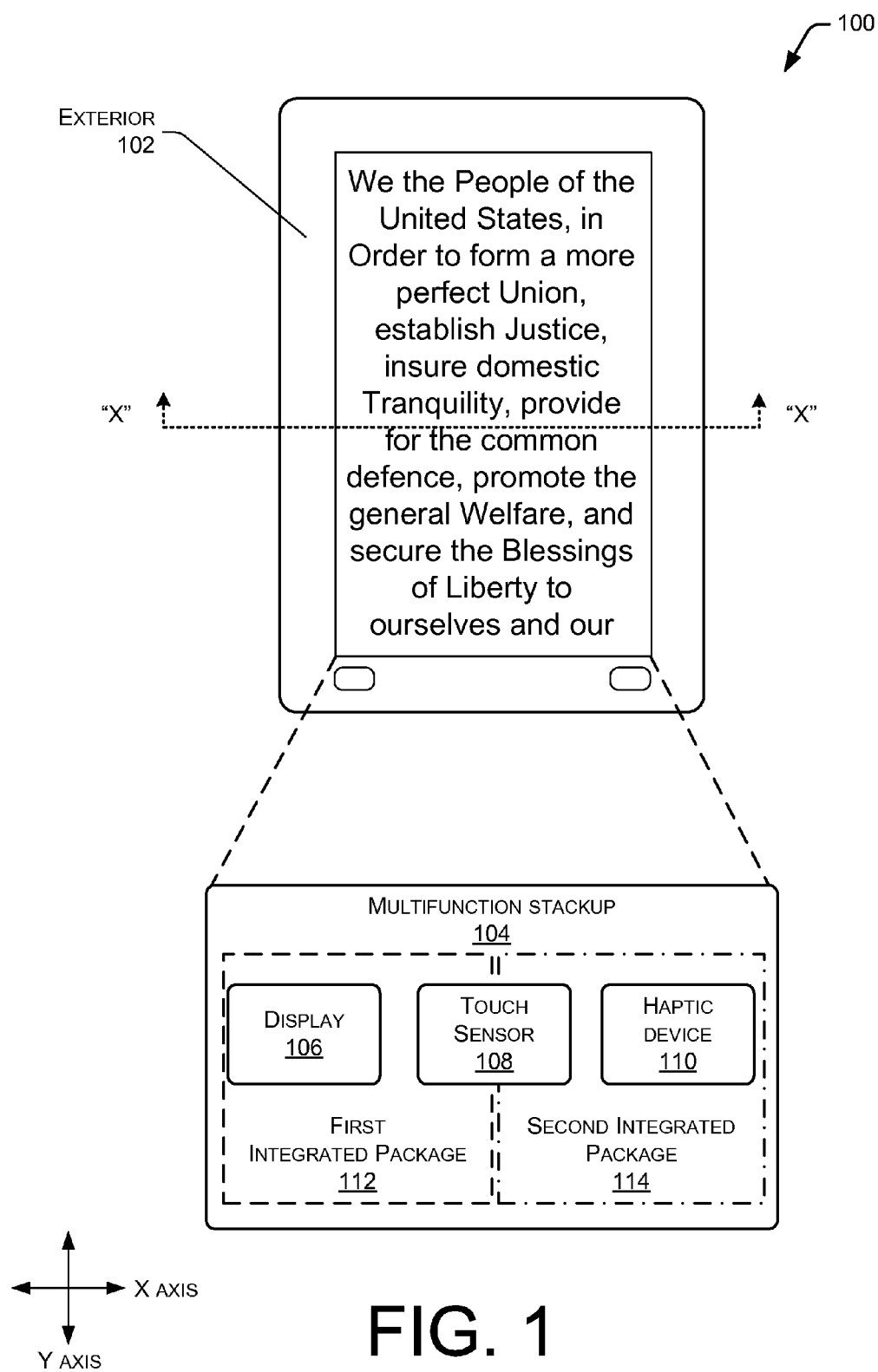
FIG. 1 depicts an illustrative electronic book ("eBook") reader device having a display, a haptic device, and a touch sensor formed from two integrated packages.

Electronic devices such as cellular phones, portable media players, tablet computers, netbooks, laptops, electronic book ("eBook") readers, and so forth, increasingly incorporate displays, touch sensors, and haptic output devices to better enable users to control and otherwise interact with the devices. For example touch screens which combine the display with the touch sensor may be further combined with haptic output devices to provide useful haptic feedback to a user. This feedback may allow the user to determine tactilely their interaction with the device. For example, the user may be able to determine based on tactile input when they have placed their finger on a control presented on the display, selected the control, deselected the control, and so forth. Traditional haptic devices provide coarse low-resolution haptic output, and are bulky and cumbersome to integrate into electronic devices, particularly thin devices with very low-profiles.

This disclosure describes, in part, an actuator tab configured to generate haptic output that is incorporated into a substrate of a component, such as a display, touch sensor, battery, and so forth. A plurality of these actuators may be used to generate high resolution haptic output. This disclosure also describes methods of assembling the actuator tabs. In some implementations, the actuator tabs may be incorporated into the substrates of components, such as those within a multifunction stackup. The multifunction stackup may include the display, the touch sensor, and the actuator tabs in a low-profile package. This discussion below also describes methods of using the actuator tabs to reduce audible output while generating haptic output.

The multifunction stackup may include a first integrated package comprising the display on a first side and a first layer of a touch sensor on a second side. In some implementations, the touch sensor may comprise an interpolating force sensing resistor (IFSR) array. A second integrated package comprises the haptic device on a first side and a second layer of the touch sensor on the second side. At the surfaces where the first and second integrated packages come together a dielectric edging and an edge seal adhesive are provided around a perimeter of the touch sensor. The dielectric edging prevents the immediate edges of the touch sensor from sticking after assembly. This sticking may result from the inherent tackiness of the touch sensor material, the edge seal adhesive intruding into the touch sensor array, or other factors.

During assembly, the first and second integrated packages may use various protective liners and release liners. For example, a film release adhesive may be used to prevent the introduction of foreign objects onto the adhesive surface. In some implementations, the adhesives used may be low tack, or otherwise designed to allow for separation after assembly. Such separation allows for rework, and aids in improving production yields and repair opportunities.

A haptic device using actuator tabs may be incorporated into the multifunction stack. This haptic device may comprise a single haptic actuator, or a plurality of actuators configured to form a high resolution haptic array. The haptic device is configured to couple the mechanical output of the haptic actuators ultimately to the user via the display, touch sensor, exterior case, and so forth. When assembled, the haptic device presents a substantially planar aspect, allowing for a smooth integration with other components. A portion of this device may act as a haptic shield, providing electrical shielding between adjacent potentially interfering components, such as a touch sensor adjacent to the haptic actuator.

Mutamorphic materials change shape upon the application of a signal. The signal may be electrical, magnetic, optical, thermal, chemical, and so forth. This change may include a contraction or expansion along one or more dimensions. For example, but not by way of limitation, mutamorphic materials include various crystals such as quartz, ceramics such as lead zirconate titanate, and polymers such as polyvinylidene fluoride, electro-active polymers, ionic polymer-metal composites, and so forth. Applying the signal to the mutamorphic material results in an alteration of the shape of the material and generation of a physical force. For example, application of an electric field to a ceramic piezoelectric material results in the alteration of the shape of the piezoelectric material. The physical force resulting from the alteration of the shape produces haptic output, suitable for use as user feedback. In this disclosure the term "piezoelectric material" is used for convenience and not by way of limitation as one example of a mutamorphic material.

Assembly of the multifunction stackup involves many components with various degrees of stiffness. For example, a substrate of the display may be relatively rigid, as may be the haptic device, while other components such as the touch sensor layers may be relatively flexible. Within the haptic device, in some implementations the material is relatively stiff in compression, compared with the touch sensor layers. Additionally, in some implementations material within the haptic device may exhibit a relatively low bending stiffness. For example, fiberglass-reinforced circuit boards of FR-4 with a height (that is, along a z-axis) of between $2/1000$ and $5/1000$ inch are suitable in some applications.

By providing additional compliance within the materials used in the haptic device as well as in the overall multifunction stackup, high-resolution haptic arrays capable of producing localized fine haptic output on the display are possible. Within the high-resolution haptic array, a plurality of haptic actuators is used to provide haptic output. In some implementations, individual actuators may be relatively small. These smaller actuators minimize power consumption and generation of noise (both electrical and mechanical), particularly when compared to larger haptic output devices. For example, rather than firing a single large actuator with a large power draw to provide haptic output in response to a fingertip touch, a smaller actuator proximate to the fingertip may be fired.

The cost and complexity of laminating components increases when trying to laminate a flexible material to another flexible material. As a result, the lamination of the first and second layers of the touch sensor may be costly due to this flexibility, and may also be prone to yield problems.

By utilizing the relative rigidity of the display and the haptic device, it is possible to minimize or avoid the problems associated with the flexible-to-flexible lamination. The relatively rigid display is laminated to a first layer of the touch sensor, forming the first integrated package described above. This (relatively) rigid-to-flexible lamination process is simpler and less costly than a flexible-to-flexible lamination. Similarly, the relatively rigid haptic device is laminated to a relatively flexible second layer of the touch sensor, forming the second integrated package described above.

Upon assembly of the first and second integrated packages (which are both relatively rigid, and thus simpler to handle) the touch sensor is formed. The first and second integrated packages may be assembled at different locations, by different suppliers, and so forth.

Haptic actuators may be placed in various positions within the haptic device, or within a device in general. In some implementations, the haptic actuators may be placed in an array. In another implementation, haptic actuators may be placed complementary to common control positions under the display. Complementary placement may be coincident with, adjacent to, or otherwise such that haptic output from the actuator manifests at or proximate to the common control position. Common control positions are those areas where the user interface typically presents a user control such as a button or slider. Haptic actuators may also be placed complementary to physical controls such as buttons.

A portion of the touch sensor may provide for dedicated buttons. This portion may be part of the regular array, or may be an extension or additional portion thereof. For example, an additional touch sensitive area may be provided which is used as a button. Some touch sensor technologies, such as IFSR, may use a cushion of air or another gas between layers. When an incident force is applied to the touch sensor, particularly within the relatively small confines of a button, internal gas pressure may build due to a reduction in volume. This buildup may result in "pillowing," blowouts of seals, and other undesirable effects. Furthermore, atmospheric pressure changes may also introduce these or other undesirable effects when the touch sensor is otherwise sealed.

As described herein, an air channel may be provided between a dedicated button which is part of the touch sensor and the main body of the touch sensor. This channel allows for the gas displaced during activation of the button to escape the immediate confines of the button into the main body of the touch sensor and minimizes adverse effects which result from pressure buildup. Additionally, gasses may be exchanged between the ambient atmosphere and the touch sensor volume via a filter and inlet/outlet open to the ambient atmosphere. This ameliorates the difficulties which may be experienced due to extreme pressure changes, such as with changes in altitude, large surface area pressures on the touch sensor, and so forth.

Given the relatively close proximity of various devices which utilize electric fields, suppression of electrical interference is desirable. For example, the electric fields generated by activation of pixels on the display may generate interference in the touch sensor, or vice versa. Similarly, the electric fields generated during use of haptic actuators may introduce noise in the touch sensor, display, or both. Conventional grounding straps between layers may provide insufficient grounding, and may also be precluded by the small form factor of the device, particularly in the case of the multifunction stackup.

Discussed in this application is the use of an integrated grounding channel which extends from a display shield through the touch sensor to the haptic shield. This grounding channel may be a hole, notch or other communicating feature into which a conductive material (such as a conductive paste) is inserted to establish the conductive pathway between the shields, chassis ground, and so forth. In some implementations, a plurality of grounding channels may extend between the display shield and haptic shield. In other implementations, the grounding channel may extend between other shields.

The multifunction stack may not always present a flat or substantially planar aspect to the user. This may result from variances in manufacture, assembly, temperature changes, and so forth. However, users find it disconcerting to touch on the surface of a touch device when the surface has "bubbles." Described herein are two methods for providing a consistent feel to the user.

A first method provides a consistent feel to the user by placing the multifunction stackup within a frame, and using attachment members to impart a tension upon the multifunction stackup. This tension pulls the multifunction stackup into a substantially planar state. A second method affixes the multifunction stackup to a backing which is slightly curved in a single plane. This slight curvature prevents separation or "bubbles" during and after assembly due to the tension between the multifunction stackup and the backing.

Haptic actuators such as those using mutamorphic materials may be activated in several states. For example, piezoelectric material may contract when applying a first polarity and expand when applying an opposite second polarity. This expansion and contraction may result in various displacements within the attached material. For example, contraction may cause a substrate to deform into a protuberance while expansion may cause the substrate to deform to an indented shape. The haptic actuators within the haptic device may thus be activated to form different mechanical deformations in the substrate. In one implementation, adjacent haptic actuators may be intentionally fired with opposite displacements to generate ridges, ripples, and so forth. Thus, haptic output may include surface features as well as vibratory effects.

A midframe may also support the elements of the multifunction stackup. The midframe is an internal structural element of the device to which other components may be affixed. The haptic actuators may be embedded, at least partially, within the midframe. In this implementation the second integrated package may thus comprise the second touch sensor layer, the midframe, and the haptic actuators embedded therein.

As described above, haptic actuators may be affixed to a core board to form a haptic device, which in turn may be laminated with other components within the stackup. As described herein, it is also possible to form haptic actuators directly onto a substrate of a component, such as the display. One or more separations or cutouts form an actuator tab within the substrate. Mutamorphic material is coupled to at least a portion of the actuator tab, forming the haptic actuator. In another implementation the actuator tab may be a separate piece coupled to the substrate, such as via adhesive, welding, mechanical fastener, and so forth.

The actuator tabs have at least one attached side forming a neck which connects with the substrate. When active, the mutamorphic material deforms the actuator tab which results in displacement of the actuator tab. The displacement predominately occurs on one or more free (or unattached) sides. The displacement resulting from this deformation is transferred by the substrate from the actuator tab into at least a portion of the substrate itself. When the actuator tabs are configured such that they are not in a plane parallel to that of the substrate, the physical displacement may be such that the direction of the displacement is within, and not orthogonal to, the plane of the substrate.

Haptic output may produce output which is audible to a user. For example, physical displacements of the substrate which are orthogonal to the plane of the substrate cause the substrate to act like the diaphragm of a speaker, producing audible output. This audible output may be undesirable for several reasons. For example, the sound may be distracting to the user, interfere with desirable audio output such as from speakers or operation of a microphone within the device, and so forth. By arranging the haptic actuator such that haptic output generates physical displacements which are in-plane and not orthogonal with the substrate, audible output may be reduced or practically eliminated. That is, the substrate may shift left and right while the actuator tab is active, but not up and down, thus reducing or essentially eliminating audible output.

Illustrative Touch-Screen Device

FIG. 1 depicts an illustrative electronic book ("eBook") reader device 100 having a display, a haptic device, and a touch sensor formed from two integrated packages. While an eBook reader device 100 is illustrated, other electronic devices may be configured as described herein. These other devices include cellular phones, portable media players, tablet computers, netbooks, laptops, and so forth. While a touch sensor comprising an interpolating force sensitive resistor (IFSR) array is described herein, other technologies such as capacitive touch sensing may be used.

FIG. 1 depicts that eBook reader device 100 includes an exterior enclosure 102. Approximately perpendicular to the long axis of the enclosure 102 is cross sectional line "X." In some implementations, as described below, haptic actuators may be coupled to the exterior 102 to provide haptic output on the exterior surface of the device.

As illustrated, eBook reader device 100 includes a multifunction stackup 104. This multifunction stackup 104 provides the functionality of at least a display 106, touch sensor 108, and haptic device 110. The haptic device 110 is configured to provide haptic output which is above a pre-determined threshold and thus perceptible to a user. The haptic device may incorporate an array of haptic actuators in a high resolution haptic array, such as described below with regards to FIG. 16.

The display 106, touch sensor 108, and haptic device 110 may be coordinated to provide an integrated user experience. For example, the display 106 may present a user control, the touch sensor 108 may detect a touch from a user corresponding to the user control, and the haptic device 110 may generate haptic output to provide feedback to the user.

In some implementations other functions and components may be incorporated into the multifunction stackup 104. The multifunction stackup 104 may be segregated into two sections: a first integrated package 112 comprising the display 106 and a first layer of the touch sensor 108, and a second integrated package 114 comprising the haptic device 110 and a second layer of the touch sensor 108. Upon assembly, the first and second integrated packages thus form the touch sensor 108.

Assembly of the multifunction stackup 104 includes placement of the first integrated package 112 proximate to the second integrated package 114. This assembly is discussed below in more detail with regards to FIGS. 2-6.

Figure 2:
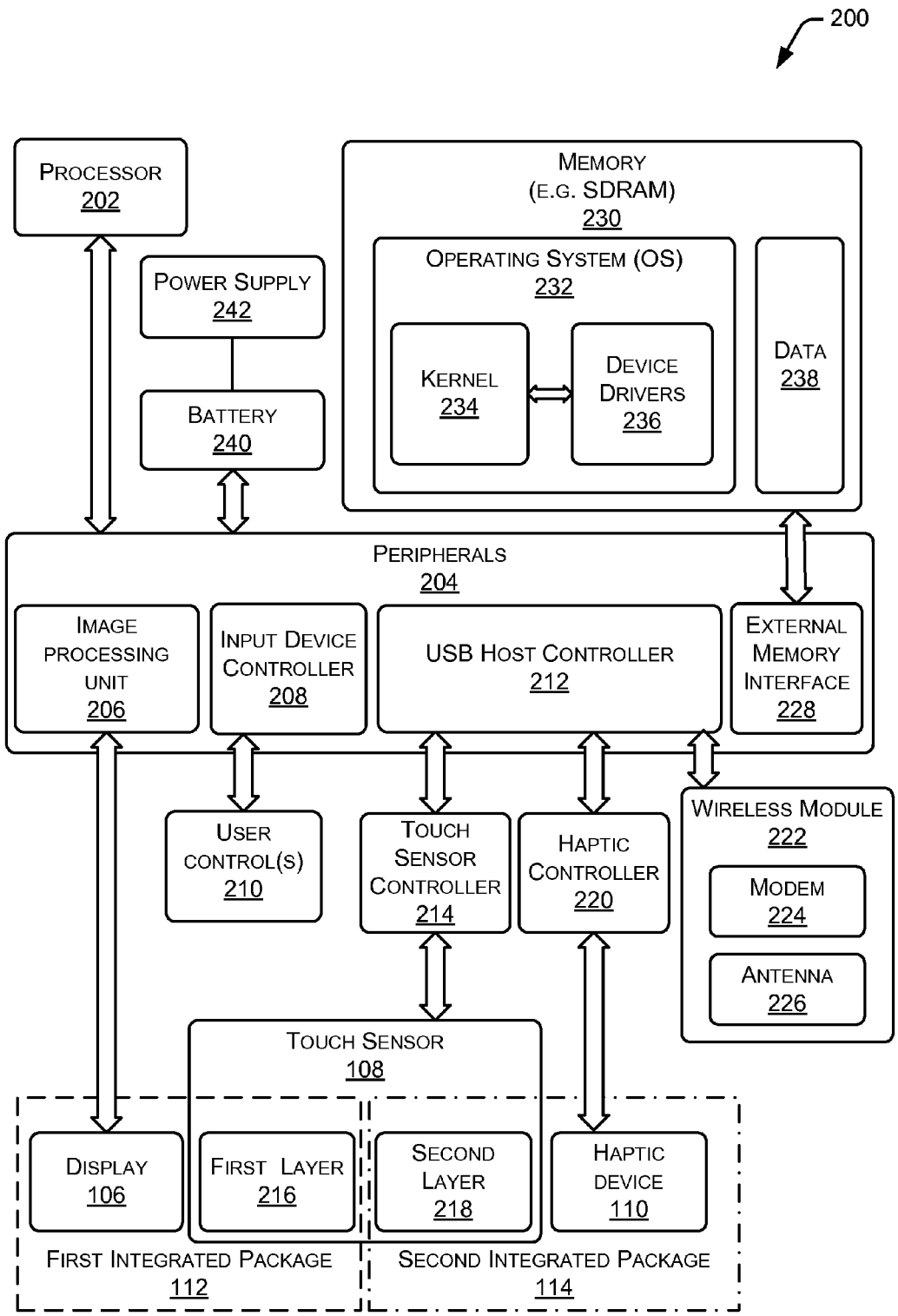
FIG. 2 is an illustrative schematic of an electronic device showing an example distribution of components across the integrated packages.

FIG. 2 is an illustrative schematic 200 of an electronic device, such as the eBook reader device 100. In a very basic configuration, the device 100 includes components such as a processor 202 and one or more peripherals 204. Each processor 202 may itself comprise one or more processors.

Peripherals 204 couple to the processor 202. An image processing unit 206 is shown coupled to one or more display components 106 (or "displays"). In some implementations, multiple displays may be present and coupled to the image processing unit 206. These multiple displays may be located in different enclosures or panels. Furthermore, one or more image processing units 206 may couple to the multiple displays.

The display 106 may present content in a human-readable format to a user. The display 106 may be reflective, emissive, or a combination of both. Reflective displays utilize incident light to present an image and include electrophoretic displays, interferometric modulator displays, cholesteric displays, pre-printed sheets, and so forth. For example, an electrophoretic display may be configured to present changeable content, such as different pages from an eBook, while a pre-printed sheet may be configured to present pre-determined content such as icons, letters, text, and so forth.

Emissive displays do not rely on incident light and, instead, emit light to present an image. Emissive displays include backlit liquid crystal displays, time multiplexed optical shutter displays, light emitting diode displays, backlit pre-printed sheets, and so forth. When multiple displays are present, these displays may be of the same or different types. For example, one display may be an electrophoretic display while another may be a liquid crystal display. The display 106 is generally flexible such that it transmits a force applied to its surface, such as a touch, to the touch sensor or a haptic output from the haptic actuator to the user.

The content presented on the display 106 may take the form of electronic books or "eBooks." For example, the display 106 may depict the text of the eBooks and also any illustrations, tables, or graphic elements that might be contained in the eBooks. The terms "book" and/or "eBook", as used herein, include electronic or digital representations of printed works, as well as content objects that may include text, multimedia, hypertext, and/or hypermedia. Examples of printed and/or digital works include, but are not limited to, books, magazines, newspapers, periodicals, journals, reference materials, telephone books, textbooks, anthologies, instruction manuals, proceedings of meetings, forms, directories, maps, web pages, and so forth. Accordingly, the terms "book" and/or "eBook" may include any readable or viewable content that is in electronic or digital form.

The device 100 further includes a touch sensitive input device. In one implementation, the touch sensor 108 may comprise an interpolating touch sensitive resistor (IFSR) array. The IFSR touch sensor may be configured to respond to the location and magnitude of an incident force applied to the touch sensor array. The IFSR array may comprise two overall layers, a first layer 216 and a second layer 218. Each of these layers may, in turn, comprise other layers such as force sensitive resistive material, conductive wires, and so forth.

For convenience only, the multifunction stackup 104, including the display 106, is shown in a generally rectangular configuration. However, it is understood that the multifunction stackup 104, display 106, touch sensor 108, and haptic device 110 may be implemented in any shape, and may have any ratio of height to width. Also, they may be curved or otherwise non-linearly shaped. Furthermore they may be flexible and configured to fold or roll.

The eBook reader device 100 may have an input device controller 208 configured to accept input from the touch sensor, keypad, keyboard, or other user actuable controls 210. These user actuable controls 210 may have dedicated or assigned operations. For instance, the actuable controls 210 may include fixed controls such as page turning buttons, navigational keys, a power on/off button, selection keys, joystick, dedicated button on the touch sensor 108, and so forth. These controls are "fixed" in the sense that they have a pre-determined physical position and manifestation. Actions associated with these controls may vary according to configuration, operating mode, and so forth.

A USB host controller 212 may also be present. The USB host controller 212 manages communications between devices attached to a universal serial bus ("USB") and the processor 202 and other peripherals. These peripherals may include a touch sensor controller 214 coupled to the processor 202 via the USB host controller 212 (as shown). In other implementations the touch sensor controller 214 may couple to the processor via the input device control 208, inter-integrated circuit ("I²C"), universal asynchronous receiver/transmitter ("UART"), or serial peripheral interface bus ("SPI"), or other interface. The touch sensor controller 214 is also coupled to components within the touch sensor 108, such as the first layer 216 and second layer 218.

The touch sensor controller 214 is configured to use the touch sensor 108 to determine characteristics of interaction with the touch sensor. These characteristics may include the location of the touch on the touch sensor 108, magnitude of the force, shape of the touch, and so forth.

A haptic controller 220 may couple the haptic device 110 to the USB host controller 212. In another implementation, the haptic controller 220 may couple to another interface within the electronic device 100. The haptic controller 220 provides drive signals which activate the haptic actuators within the haptic device 110. The haptic actuators are configured to generate a haptic output which may be felt by the user. The haptic output, for example, may simulate the tactile experience of the user pushing a button presented on the display 106 as if the button were an actual mechanical button.

A wireless module 222 may couple to the USB host controller 212 via the universal serial bus. The wireless module 222 may allow for connection to wireless local area networks ("WLANs") or wireless wide area networks ("WWANs"). The wireless module 222 may include a modem 224 configured to send and receive data wirelessly; as well as one or more antennas 226 suitable for propagating a wireless signal. In other implementations, a wired network interface may be provided.

The eBook reader device 100 may also include an external memory interface ("EMI") 228 coupled to external memory 230. The EMI 228 manages access to data stored in external memory 230. The external memory 230 may comprise Static Random Access Memory ("SRAM"), Pseudostatic Random Access Memory ("PSRAM"), Synchronous Dynamic Random Access Memory ("SDRAM"), Double Data Rate SDRAM ("DDR"), Phase-Change RAM ("PCRAM"), or other computer-readable storage media.

The external memory 230 may store an operating system 232 comprising a kernel 234 operatively coupled to one or more device drivers 236. The device drivers 236 are also operatively coupled to the peripherals 204. The external memory 230 may also store data 238, which may comprise content objects for consumption on eBook reader device 100, executable programs, databases, user settings, configuration files, device status, and so forth.

One or more batteries 240 provide operational electrical power to components of the eBook reader device 100 for operation when the device is disconnected from a power supply 242. Operational electrical power is sufficient to provide for operation of the device, as distinguished from the lesser electrical power requirements of a sleep or state retention mode.

The power supply 242 may be internal or external to the eBook reader device 100. The power supply 242 is configured to provide operational power for eBook reader device 100, charge the battery 240, or both. "Battery" as used in this application includes components capable of acting as a power source to an electronic device. Power sources include chemical storage cells such as lithium polymer batteries, charge storage devices such as ultracapacitors, fuel cells, and so forth.

Furthermore, the eBook reader device 100 may include one or more other, non-illustrated peripherals, such as a hard drive using magnetic, optical, or solid state storage to store information, a firewire bus, a Bluetooth™ wireless network interface, a camera, an accelerometer, an ambient light sensor, a global positioning system, a PC Card component, and so forth.

Couplings between the illustrated components are shown for emphasis, and not by way of limitation. There are couplings between many of the components illustrated in FIG. 2, but graphical arrows are omitted for clarity of illustration.

Illustrative Devices

For clarity of illustration the proportions and dimensions of the various components may be exaggerated or understated. Unless otherwise indicated, the following figures are not drawn to scale and the components, unless specifically noted, are not necessarily proportionate to one another. Furthermore, while some particular materials are mentioned, it is understood that other materials may be utilized. For example, while copper is mentioned, in other implementations other conductive materials such as conductive polymers, other metals, and so forth may be used. The properties of specific materials mentioned herein are those as of the filing date.

In some implementations flexible printed circuits (FPCs) may be used to connect a component such as the display 106, touch sensor 108, haptic device 110, and so forth to an associated controller or other component. The flexible printed circuits may be bonded to complementary points on the component, then wrapped or folded around the edges of the component to allow for the routing. The other end of the FPC may then be bonded, placed into a zero-insertion force socket, or placed into another socket to establish an electrical connection. Such an arrangement allows for a high connector density while minimizing usage of connector space on a circuit board.

Figure 3:
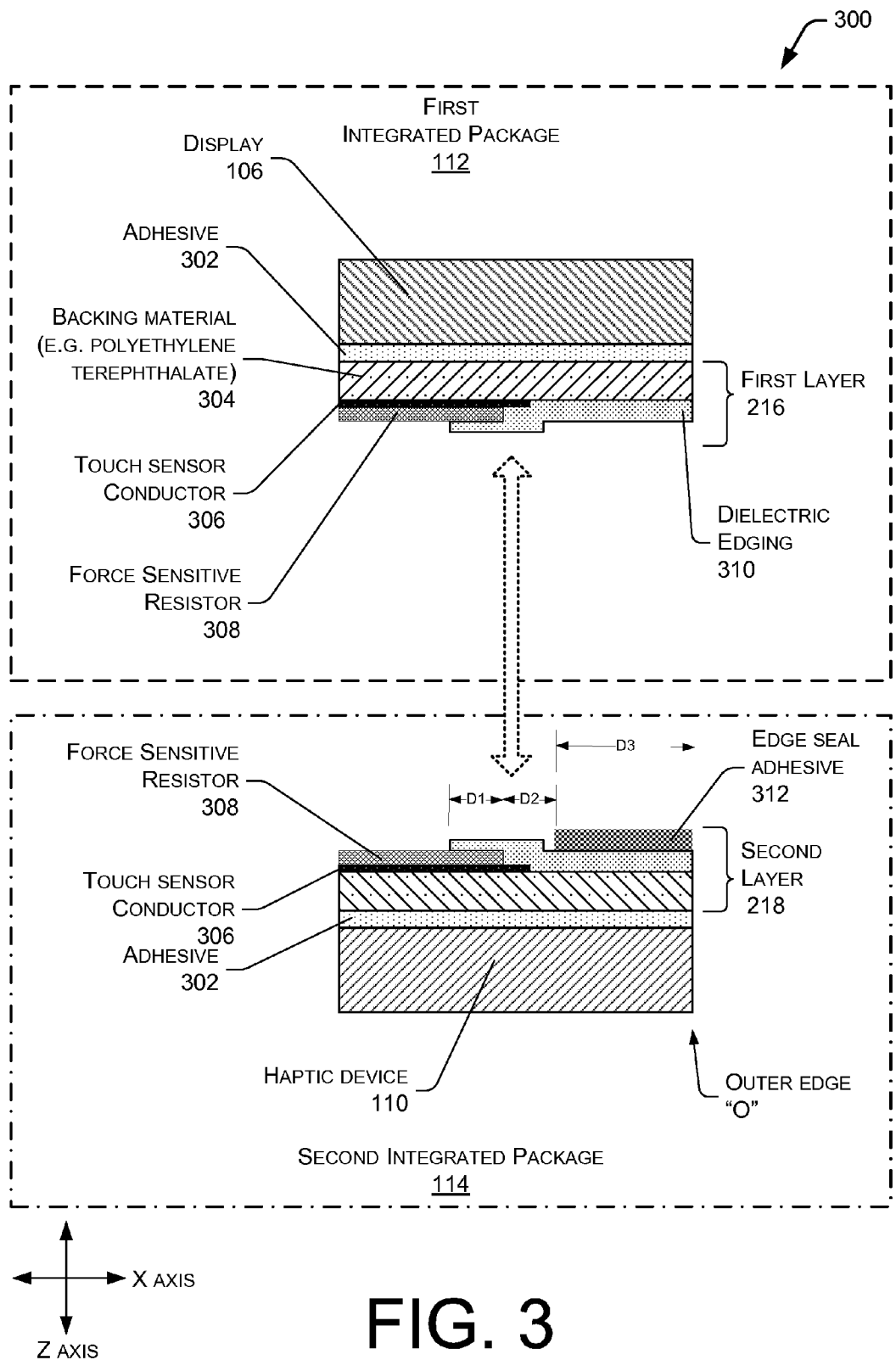
FIG. 3 illustrates a cross section of a multifunction stackup having two integrated packages with dielectric edging and an edge seal adhesive which may combine to form the touch sensor.

FIG. 3 illustrates a cross section 300 of the multifunction stackup 104. As shown here, the two integrated packages 112 and 114 may be joined along the direction indicated by the arrow to form the multifunction stackup 104.

A display 106 is shown coupled via an adhesive 302 to a backing material 304. The backing material 304 acts as a substrate for the first layer 216 of the touch sensor 108. The backing material 304 may comprise polyethylene terephthalate ("PET"). The first layer 216 of the IFSR touch sensor may comprise one or more touch sensor conductors 306, force sensitive resistors 308, and other components affixed or deposited to the backing material 304. In some implementations the backing material 304 and adhesive 302 may be omitted and the touch sensor conductor 306, force sensitive resistor 308, and other touch sensor 108 components may be deposited or affixed directly to the display 106. In another implementation, the display 106 may incorporate a conductive area as a display shield to act as an electrical shield to reduce or eliminate electromagnetic interference between the adjacent components.

Disposed around a perimeter of the touch sensor 108 is dielectric edging 310. The dielectric edging 310 extends from an outer edge "O" of the touch sensor perimeter over a portion of the touch sensor components.

An edge seal adhesive 312 is used upon assembly to join the first integrated package 112 and the second integrated package 114. Once joined, the touch sensor 108 is formed and the multifunction stackup 104 is complete.

The dielectric edging 310 which extends over a portion of the touch sensor components prevents the edges of the touch sensor from sticking when a force is applied. For example, a user may touch a stylus to the edge of the screen, pushing the first and second layers together. The dielectric edging provides some distance D1 and D2 between the point of contact on the touch sensor and the edge seal adhesive 312. When released, the first and second layers of the touch sensor may again separate and resume their previous state. In some implementations D1 and D2 may be about 1 millimeter (mm) wide each while a width D3 of the edge seal adhesive 312 may be about 3.25 mm. In other implementations, these dimensions may vary.

Alignment between the integrated packages 112 and 114, and for layers therein, may be accomplished via optical, mechanical, or other registration techniques. In one implementation, optical alignment marks may be provided and used for positioning layers. In another implementation, registration features may be incorporated into the layers to aid proper alignment during assembly.

FIG. 4 illustrates a cross section 400 of the multifunction stackup 104 of FIG. 3 when the two integrated packages 112 and 114 are joined via an edge seal adhesive 312. Portions of the dielectric edging 310 which extend over the touch sensor 108 are now in contact. In some implementations, such as in some IFSR sensors, a small gap 402 is maintained between the first and second layers of the touch sensor 108. This gap within the touch sensor 108 defines a volume which may be filled with a gas, such as ambient atmosphere during the time of assembly.

In another implementation, an edge seal gasket or non-adhesive material may be used. In such an implementation, the first and second integrated packages 112 and 114, respectively, may be joined using mechanical fasteners such as clips, screws, bolts, and so forth. Such an implementation allows for easier separation of the first and second integrated packages in the event rework or repair is called for.

Figure 5:
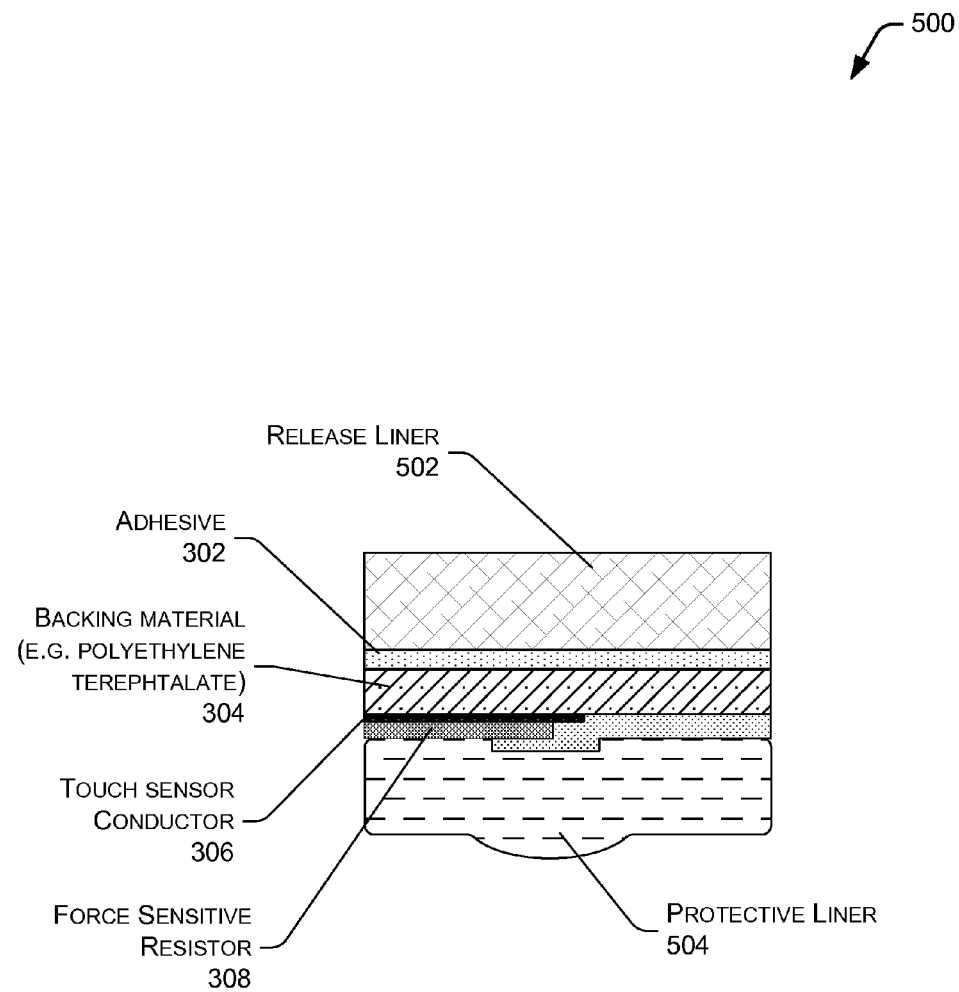
FIG. 5 illustrates a cross section of the first integrated package prior to assembly, with protective and release liners affixed.

FIG. 5 illustrates a cross section 500 of the first integrated package 112 prior to assembly. A release liner 502 is shown adjacent to the adhesive 302. Removed before assembly, the release liner leaves behind a layer or film of adhesive and while in place protects the component during handling. Placement of the adhesive as a film with a release liner prevents contamination during removal, such as may occur when a paper backing is used. Contamination may result in bubbling or other defects which may produce an undesirable seal. In one implementation, the adhesive 302 and release liner 502 may be part number 467MPF Adhesive Transfer Tape from the 3M corporation of Minnesota, United States of America.

Also shown in this cross section 500 is a protective liner 504 covering a lower section of the first integrated package 112 before assembly. The protective liner 504 prevents contamination and damage to the first touch sensor layer 216 during pre-assembly handling. The protective liner 504 acts as a temporary protective layer, and does not deposit an adhesive. In one implementation, the protective liner 504 may be part number 2112C low-tack polyethylene protective tape or film from the 3M corporation of Minnesota, United States of America.

Figure 6:
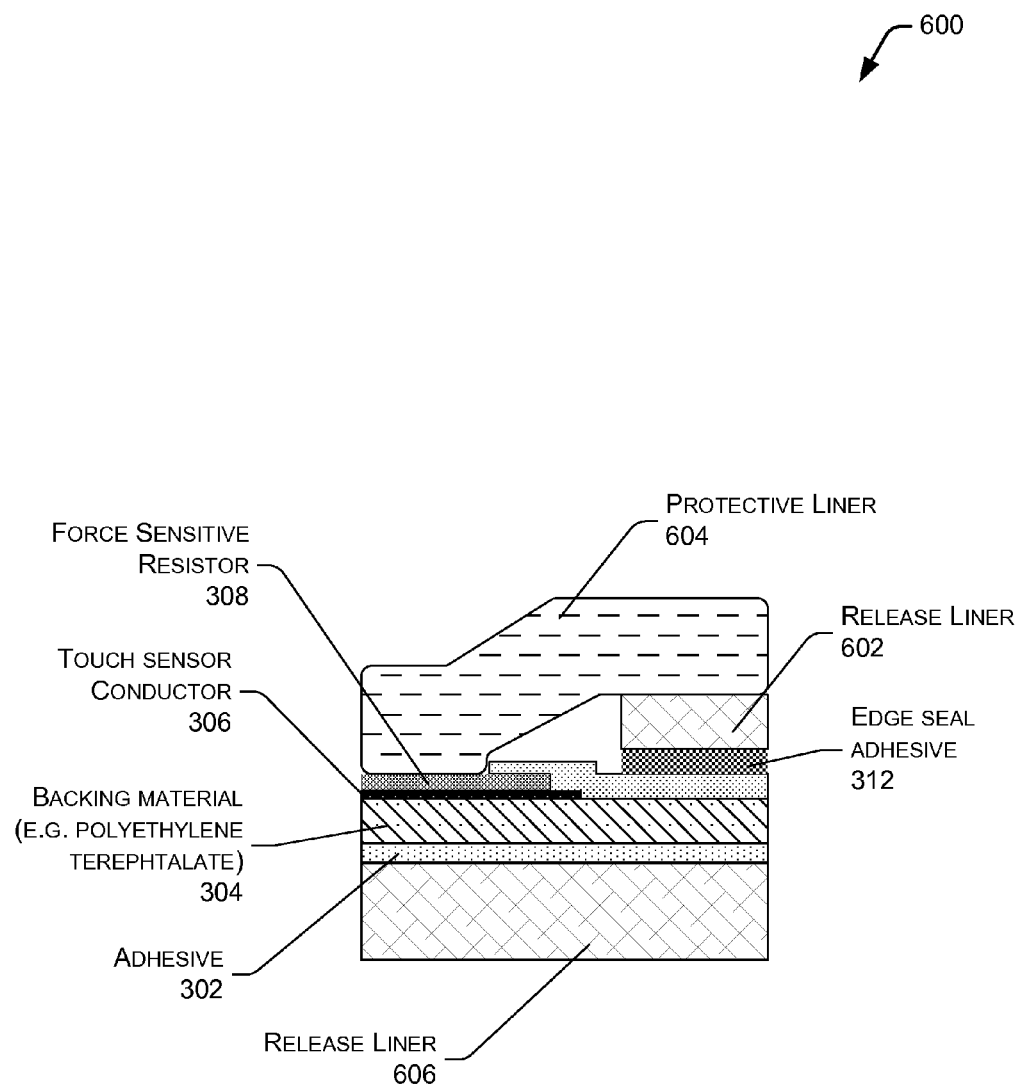
FIG. 6 illustrates a cross section of the second integrated package with protective and release liners affixed prior to assembly.

FIG. 6 illustrates a cross section 600 of the second integrated package 114 before assembly. In this figure, a release liner 602 is shown with the edge seal adhesive 312. In some implementations, the edge seal adhesive 312 may comprise part number 9457 Adhesive Transfer Tape from 3M with its corresponding release liner.

A protective liner 604 may be applied to protect the second touch sensor layer 218 during handling. In some implementations the protective liner 604 may also comprise part number 2112C low-tack polyethylene protective tape or film from 3M corporation of Minnesota, United States of America.

The adhesive 302 may be applied to the bottom of backing material 304 via a release liner 606. In one implementation, this release liner 606 may comprise part number 467MPF Adhesive Transfer Tape from the 3M corporation of Minnesota, United States of America.

Figure 7:
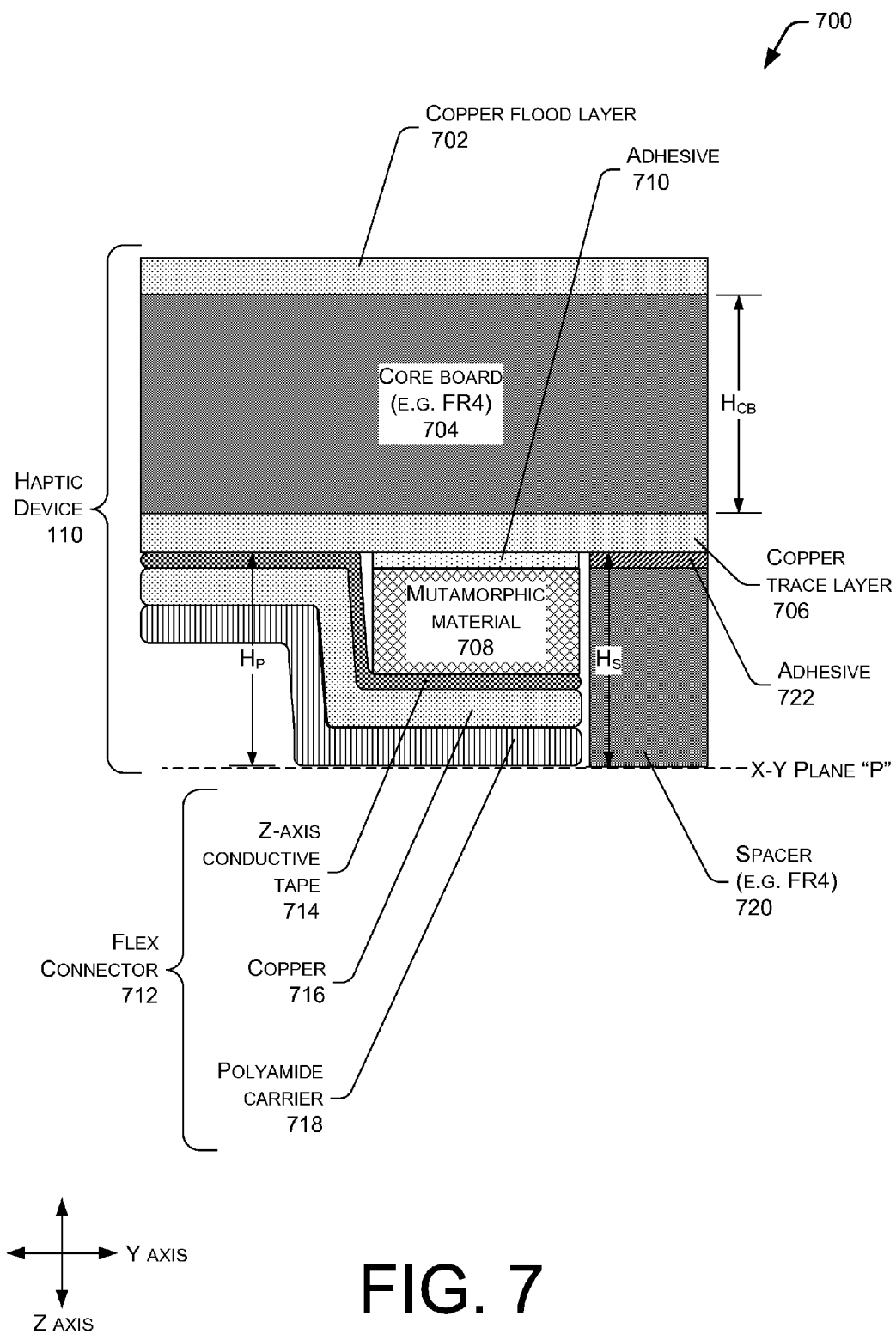
FIG. 7 illustrates a cross section of a haptic device.

FIG. 7 illustrates a cross section 700 of a portion of the haptic device 110. The haptic device 110 may comprise one or more haptic actuators which comprise mutamorphic materials, with a single example shown here. Mutamorphic materials change shape in response to a signal. For example, piezoelectric materials expand, contract, or both upon the application of an electric field. As described above, mutamorphic materials may include various crystals such as quartz, ceramics such as lead zirconate titanate, polymers such as polyvinylidene fluoride, ionic polymer-metal composites, and so forth. Applying a signal to the mutamorphic material results in an alteration of the shape of the material and generation of a physical force. The resulting physical force produces haptic output, suitable for user feedback.

The haptic device 110 may be used as a separate unit or combined with other components and devices, such as within the multifunction stackup 104. When used in proximity to other devices, electrical shielding prevents interference both to and from the activation of the haptic actuators. As shown in this figure, a copper flood layer 702 is placed at a top of the haptic device 110. This copper flood layer 702 may be coupled to an electrical ground of the device 100, to provide for electrical shielding. In one implementation a grounding channel, such as the one described below with regards to FIG. 20, may provide the coupling.

The copper flood layer 702 is affixed to a core board 704. The core board 704 comprises a material of suitable physical properties to transfer vibrations and mechanical deformations from the haptic actuator to the user. For example, the material may be relatively stiff, yet sufficiently resilient to regain a substantially pre-deformation shape upon discontinuing the application of force from one or more haptic actuators. In some implementations the core board may comprise fiberglass-reinforced circuit boards of FR-4 (FR) with a height $H_{CB}$ of between $2/1000$ and $5/1000$ of an inch. In other implementations the core board may comprise a metal, such as magnesium, aluminum, titanium, steel, and so forth.

Affixed or deposited on the bottom of the core board 704 in some implementations is a copper trace layer 706. This trace layer provides at least a portion of the electrical pathways necessary for the activation of mutamorphic material 708. As described above, the mutamorphic material 708 may comprise one or more materials configured to change shape upon application of a signal. When the material changes shape a mechanical signal is generated.

The mutamorphic material 708 is affixed or deposited to the copper trace layer 706. In some implementations the mutamorphic material 708 is affixed or deposited directly to the core board 704. In the implementation shown here, an adhesive 710 may be used to couple the mutamorphic material 708 to the copper trace layer 706. The adhesive 710 may be non-compliant, rigid, or otherwise suited to minimize or eliminate slippage between the bonded surfaces and the mutamorphic material 708. This non-compliance allows for better transfer of motion from the mutamorphic material 708 to the core board 704.

A flex connector 712 couples the mutamorphic material 708 to a trace on the copper trace layer 706. This flex connector may comprise a z-axis conductive tape 714, a copper conductor 716, and a polyamide carrier 718. The z-axis conductive tape 714 is proximate to and in contact with the mutamorphic material 708 and the copper trace layer 708, while the copper trace layer 716 is also in contact with the polyamide carrier 718. The flex connector 712 carries the signal to activate the mutamorphic material 708 and because of its flexibility maintains its coupling during motion of the mutamorphic material 708. Also shown is an overall height "$H_P$" of the mutamorphic material 708, associated adhesive 710, and the flex connector 712.

A spacer layer 720 is also shown which is affixed to the copper trace layer 706 or the core board 704 via an adhesive 722. In some implementations the spacer layer 720 may comprise FR4. The spacer layer 720 may be configured in one or more pieces having holes, cutouts, and so forth to allow for the positioning of the mutamorphic material 708, flex connectors 712, and so forth. A height of the spacer layer 720 "$H_S$" is configured such that when emplaced, a generally planar surface is provided along the X-Y plane "P". Stated another way, the height of the spacer $H_S$ is substantially the same the overall height $H_P$ of the haptic actuators and associated flex connectors on the same side of the core board 704.

When assembled, the haptic device 110 provides a substantially planar profile in the X-Y planes on both the top side (with the copper flood layer 702) and the bottom side (with the spacer 720). This allows improved integration into devices, and provides a smooth foundation for the touch sensor 108, and display 106.

FIGS. 8-12 illustrate plan views of the haptic device of FIG. 7 as successive components are affixed. In FIG. 8, the copper flood layer 702 is shown. In some implementations, the copper flood layer 702 may act as a haptic shield, providing an electrical shield between the haptic actuators and other components within the device, such as the touch sensor 108 and the display 106. In some implementations, this shield may be coupled to a display shield via a grounding channel as described below with regards to FIG. 20.

Figure 9:
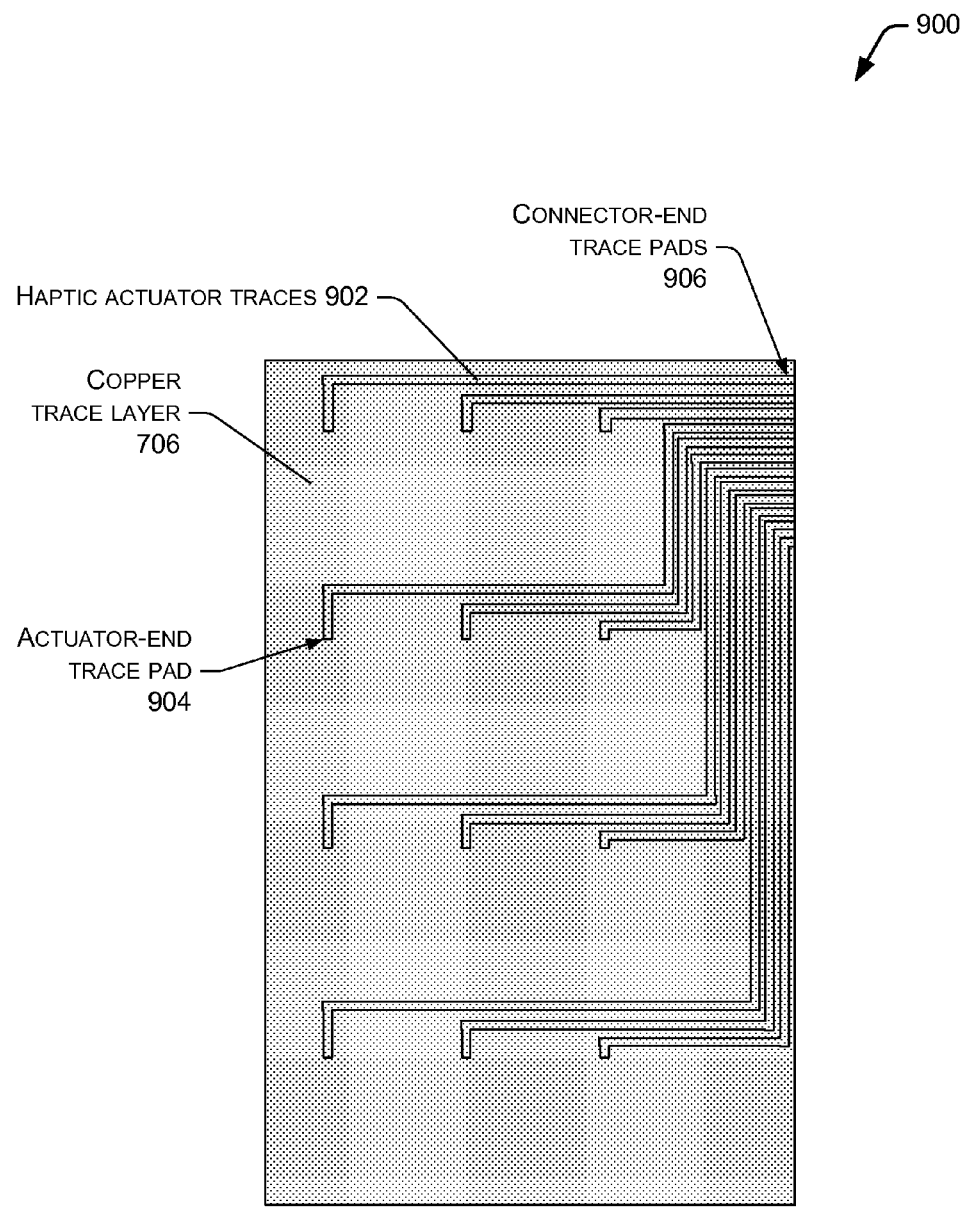

FIG. 9 illustrates the layout of traces on the copper trace layer 706. Traces may be deposited, etched, or otherwise formed. Haptic actuator traces 902 are provided. These traces 902 may have a actuator-end trace pad 904 suitable for coupling to the flex connector 712, as well as a connector-end trace pad 906 suitable for coupling to a connector (such as a flexible printed circuit) which may in turn couple to the haptic controller 220.

FIG. 10 illustrates the placement of the spacer 720 on the copper trace layer 706. Visible through cutouts are the copper trace layer 706, actuator-end trace pad 904, and connector end trace pads 906.

FIG. 11 illustrates the haptic device 110 after the mutamorphic material 708 has been deposited on the copper trace layer 706. FIG. 12 in turn shows the haptic device 110 when the flex connectors 712 have been emplaced, coupling the mutamorphic material 708 with the actuator-end trace pad 904.

Illustrative Processes

The processes described in this disclosure may be implemented by the architecture described herein or by other architectures. Each process or sub-process is illustrated as a collection of blocks in a logical flow graph, which represent a sequence of operations that can be implemented during assembly, in hardware, software, or a combination thereof. In the context of software, the blocks represent computer-executable instructions that may be stored on one or more computer-readable storage media and that, when executed by one or more processors, perform the recited operations.

Generally, computer-executable instructions include routines, programs, objects, components, data structures, and the like that perform particular functions or implement particular abstract data types. The order in which the operations are described is not intended to be construed as a limitation, and any number of the described blocks can be combined in any order or in parallel to implement the processes. It is also understood that in some implementations various steps in the processes may be omitted, or their order changed.

Figure 13:
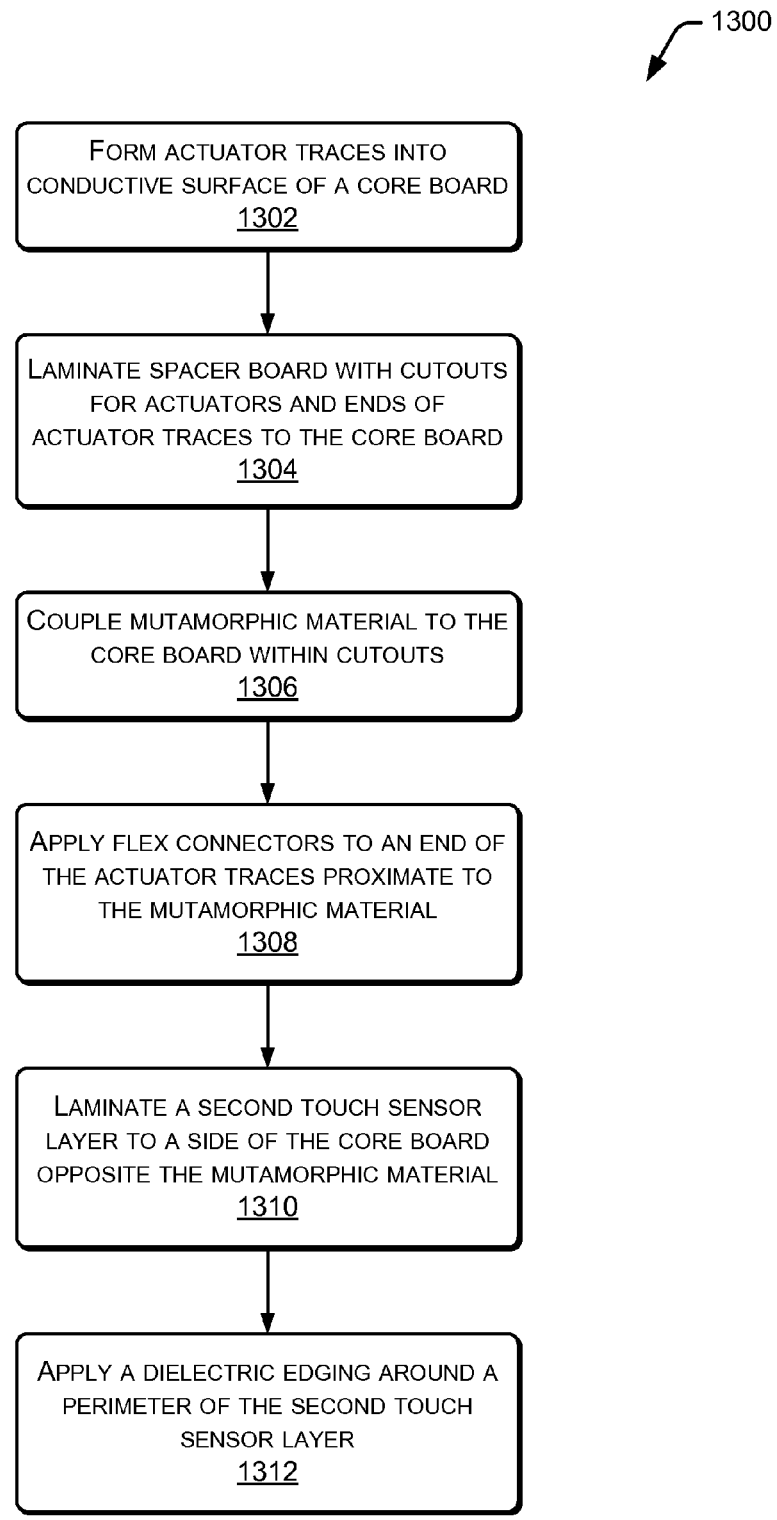
FIG. 13 is an illustrative process of assembling a haptic device.

FIG. 13 is an illustrative process 1300 of assembling the haptic device 110. At 1302, actuator traces such as the haptic actuator traces 902 are formed on or into the core board 704. For example, the traces may be etched, cut, deposited, and so forth. In some implementations, an opposite side of the core board may by configured with a conductor to act as a haptic shield, such as the copper flood layer 702.

At 1304, the spacer 720 with cutouts for the actuators and trace pads is laminated to the core board 704. The spacer 720 may comprise a single piece, or a plurality of pieces. The height of the spacer 720 is configured such that when combined with the actuators, a substantially planar surface results.

At 1306, the mutamorphic materials 708 are coupled to the core board 704 within the cutouts in the spacer 720. This coupling may comprise the adhesive 710, direct deposition, baking, and so forth. In some implementations, the mutamorphic material 708 may be coupled prior to the lamination of the spacer 720.

At 1308, the flex connectors 712 couple actuator-end trace pads 904 to the mutamorphic material 708 forming the haptic actuators. The completed assembly comprises the haptic device 110 and presents a substantially planar profile that is suitable for use with a touch sensor.

At 1310, the second touch sensor layer 218 is laminated to a side of the core board opposite the mutamorphic material 708. For example, as described above with respect to FIGS. 3-6, a backing material 304 carrying the touch sensor conductor 306 and the force sensitive resistor 308 may be laminated to the core board 704 with the adhesive 302. In some implementations the second touch sensor layer 218 may be laminated to the same side of the core board 704 as the mutamorphic material 708.

At 1312, the dielectric edging 310 is applied around a perimeter of the second touch sensor layer 218. The dielectric edging 310 thus forms a ring around the touch sensor layer.

Figure 14:
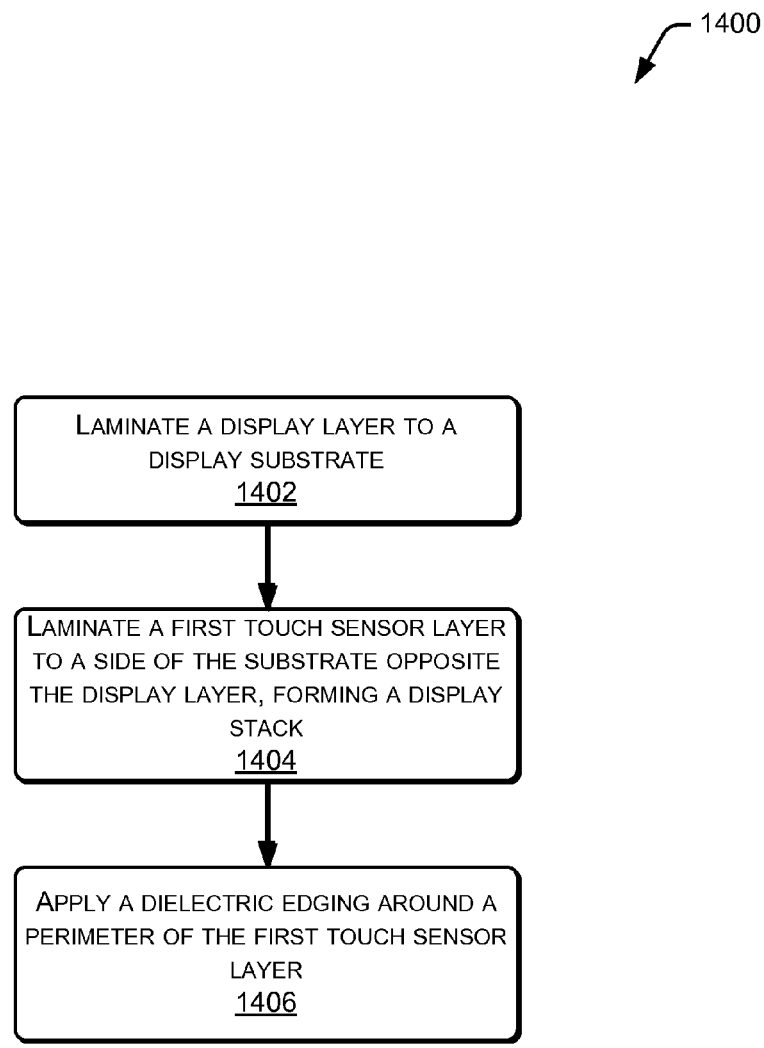
FIG. 14 is an illustrative process of assembling a display stack.

FIG. 14 is an illustrative process 1400 of assembling a display stack. At 1402, a display layer is laminated to a display substrate. For example, a front panel laminate comprising an electrophoretic slurry may be laminated to a substrate comprising drive electronics configured to affect the electrophoretic slurry.

At 1404, the first touch sensor layer 216 is laminated to a side of the display substrate opposite the display layer. In some implementations, the resulting display stack may also comprise a conductive layer to act as an electrical display shield. In some implementations, this shield may be coupled to ground such as via the grounding channel as described below with regards to FIG. 20.

At 1406, the dielectric edging 310 is applied around a perimeter of the first touch sensor layer 216. The dielectric edging 310 thus forms a ring around the touch sensor layer 216. As described above with respect to FIGS. 3-4, this prevents sticking of the touch sensor layers upon application of an incident force.

Figure 15:
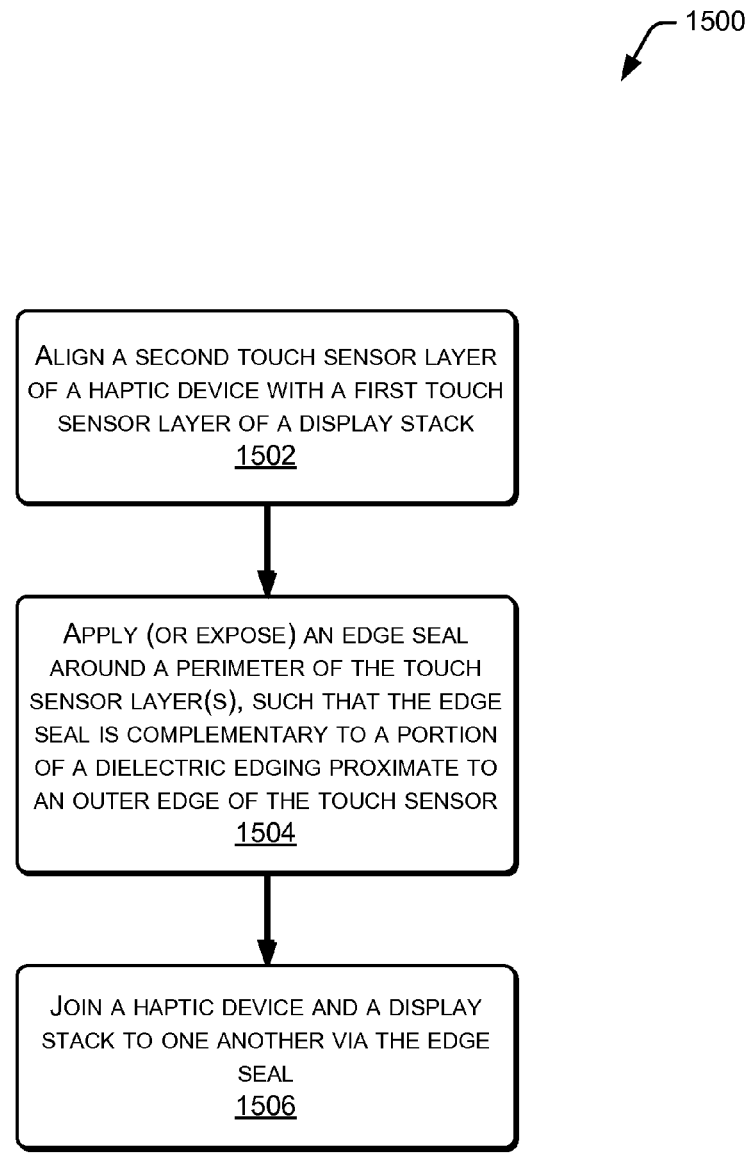
FIG. 15 is an illustrative process of assembling the multifunction stack by combining a previously assembled haptic device and a previously assembled display stack to form a touch sensor.

FIG. 15 is an illustrative process 1500 of assembling the multifunction stack 104 by combining a previously assembled first integrated package 112 with the display 106 and a previously assembled second integrated package 114 with the haptic device 110 to form the touch sensor 108.

At 1502, the first touch sensor layer 216 affixed to the display stack is aligned with the second touch sensor layer 218 affixed to the haptic device 110. This alignment may be by way of optical markings, engagement of physical features, and so forth.

At 1504, an edge seal is applied (or exposed) around a perimeter of the touch sensor layers such that the edge seal adhesive 312 is complementary to a portion of the dielectric edging 310 that is proximate to an outer edge of the touch sensor 108.

At 1506, the haptic device and the display stack are joined via the edge seal adhesive 312. In other implementations the join may be accomplished via mechanical fasteners, welding, and so forth.

Haptic Array

Different grades of haptic output may be generated by devices and perceived by users. Coarse haptic output, such as a vibration of the entire device may be perceptible by the user, but conveys only limited meaning. For example, a vibrating pager attached to the user's belt may be perceived by the user, but the vibration provides only limited information, e.g., that of an incoming message.

In contrast, fine haptic output engages more of the user's tactile senses and provides the opportunity to convey more tactile information to the user. Such fine haptic output may be more localized to a particular portion of the device and may include vibration as well as surface features. For example, the fine haptic output of some implementations described herein is capable of generating variations in the surface such as changes in elevation which are perceptible to the user, as well as vibratory effects. Thus, the fine haptic output described herein may generate a bump or ridge to tactilely signify the presence of a user control and produce a vibratory output to indicate activation.

The use of fine haptic output allows the transmission of more information to the user than is available with coarse haptic output. For example, recalling the pager example discussed above, the fine haptic output may comprise generation of a particular shape on the device to convey an identity of the incoming message's sender while the particular location on the device denotes a relative urgency of the message.

A high resolution haptic array containing two or more haptic actuators may be used to generate coarse as well as fine haptic output. In particular, the fine haptic output provides more naturalistic feedback for users, which may improve human-device interactions.

Figure 16:
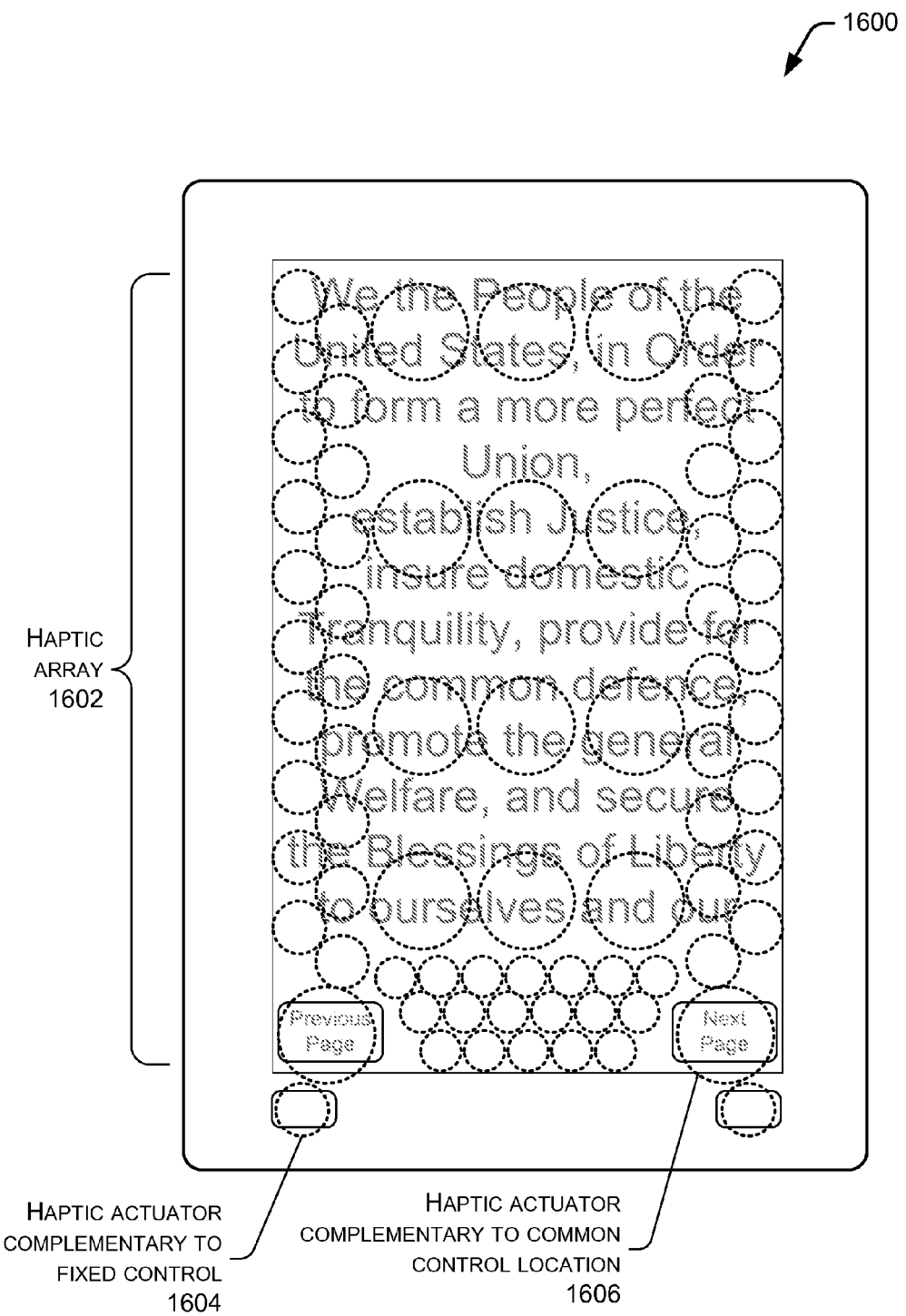
FIG. 16 illustrates locations of haptic actuators within a haptic array, as well as the positioning of haptic actuators complementary to common control positions and fixed controls.

FIG. 16 illustrates locations 1600 of haptic actuators within the device 100. A plurality of haptic actuators may form a haptic array 1602, to provide for higher resolution fine haptic output. The haptic actuators within the array 1602 may be distributed in a symmetrical arrangement, or asymmetrically as shown in this figure.

The high resolution haptic array 1602 depicted here provides the ability to produce fine haptic events at particular locations, such as corresponding with particular controls presented upon the display. These haptic events may comprise vibrations, deformations or a combination thereof of at least a portion of the device. While circular haptic actuators are shown, in other implementations the haptic actuators may be implemented in various other shapes.

Haptic actuators may be placed complementary to fixed controls 1604. Without a haptic actuator, some fixed controls may provide little user feedback. For example, a button formed from a portion or extension of the touch sensor 108 (see FIG. 19) may provide minimal or no haptic user feedback compared to a mechanical switch. Placement of a haptic actuator complementary to the fixed control 1604 such as a button may thus be used to provide feedback to the user as to when the button has been activated.

Haptic actuators may also be placed complementary to common control positions within the device. For example, the bottom section of the display 106 may be commonly used to present user actuable controls such as page turning buttons and a keypad or keyboard. A haptic actuator may be placed complementary to one or more of these common control positions 1606. As a result, high resolution haptic output may be generated which corresponds to "soft" or "virtual" controls that are rendered by the display 106 at these positions.

Placement of the haptic actuator proximate to the location where controls are commonly presented allows for improved haptic output by minimizing the distance and amount of material through which the haptic output is transferred. For example, haptic actuators may be distributed at positions where keypads or keyboards are likely to be presented to the user. Thus, in devices which support multiple orientations, clusters of haptic actuators may be provided to account for controls that are repositioned after an orientation change. For example, haptic actuators configured to support a virtual keyboard may be arranged on two or more edges to support repositioning from one edge of the device to another following a change from portrait to landscape mode.

Proximity of haptic actuators to common control locations may be physical or mechanical. Physical proximity involves spatial placement of the haptic actuator immediately beneath the common control location. Activation of the haptic actuator thus produces a haptic output which is perceived in that particular location.

Haptic actuators may also be mechanically proximate. A mechanically proximate actuator is one that is not spatially adjacent to the common control location, but rather uses a member to convey the haptic output to the particular location associated with the common control location. For example, a rigid member may convey the haptic output from a haptic actuator located to the side of the device in to a particular common control location. Such mechanical proximity may be used where haptic output is desired for a particular location, but the haptic actuator may not be located spatially adjacent due to volumetric, electromagnetic interference, constraints.

The relatively high density of many haptic actuators, such as those shown in this figure, allows for a localized deformation and thus high-resolution localized haptic effects. For example, the user may activate the "previous page" control as shown in this figure with a thumb of a left hand for which a corresponding haptic output is generated. The localization of the haptic effect provides haptic output that is above a pre-determined detection threshold and thus perceptible to the user proximate to the activated control. Because the effect is localized, the haptic output is significantly decreased. This may result in haptic output that is below the pre-determined detection threshold. As a result a finger contacting the device elsewhere, such as adjacent to the "next page" control, feels very little or no haptic output.

The haptic array 1602 with a plurality of haptic actuators also reduces power requirements and electromagnetic interference associated with the use of a single haptic actuator.

For example, rather than activating a single large haptic output device to generate haptic output above the predetermined detection threshold at a particular location, a physically smaller haptic actuator within the haptic array 1602 which is proximate to the particular location may be activated with a corresponding reduction in power consumption. Additionally, the smaller individual haptic devices of the haptic array 1602 generate less electromagnetic interference when activated singly or in small clusters than the single large actuator when activated.

Figure 17:
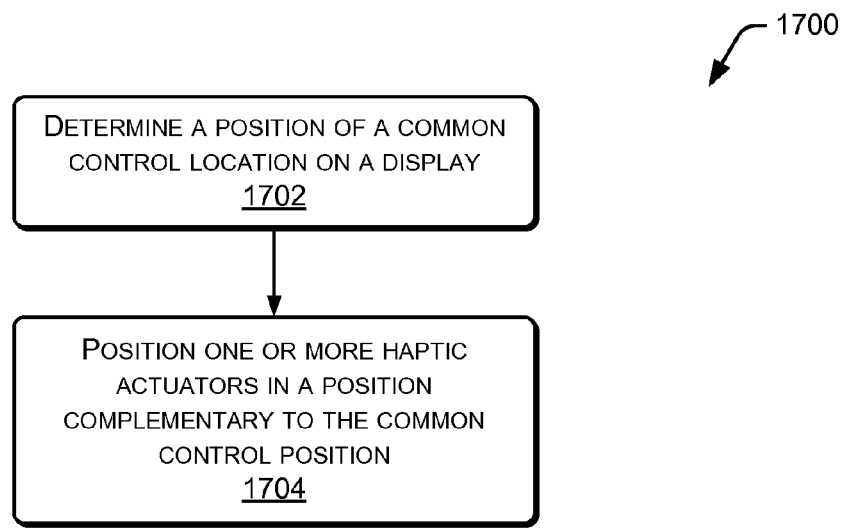
FIG. 17 is an illustrative process of positioning one or more haptic actuators adjacent to a common control position on a display.

FIG. 17 is an illustrative process 1700 of positioning one or more haptic actuators adjacent to a common control position on a display. The common control locations, as described above are positions on the device which are commonly associated "soft" or "virtual" buttons or other controls. For example, the common control may comprise a representation of a slider, push button, toggle switch, pull-down list, and so forth.

At 1702, a position of a common control position on a display 106 is determined. This common control position is where user actuable controls may be assigned for use. For example, the corners of the touch sensor 108 may be designated as positions where controls are configured. In some implementations, a visual representation of the control may be presented at a corresponding position on the display 106. Controls are not limited to these common control positions. Thus, in the case of a user interface with a large number of control elements, controls may be presented in positions that are not associated with an emplaced haptic actuator.

At 1704, one or more haptic actuators are positioned complementary to the determined common control position. For example, the one or more haptic actuators may be positioned within the array 1602 of the haptic device 110 such that when the multifunction stack 104 is assembled, the one or more haptic actuators are below the common control position. In other implementations, discrete haptic actuators or haptic actuators integrated with other components may also be used.

Figure 18:
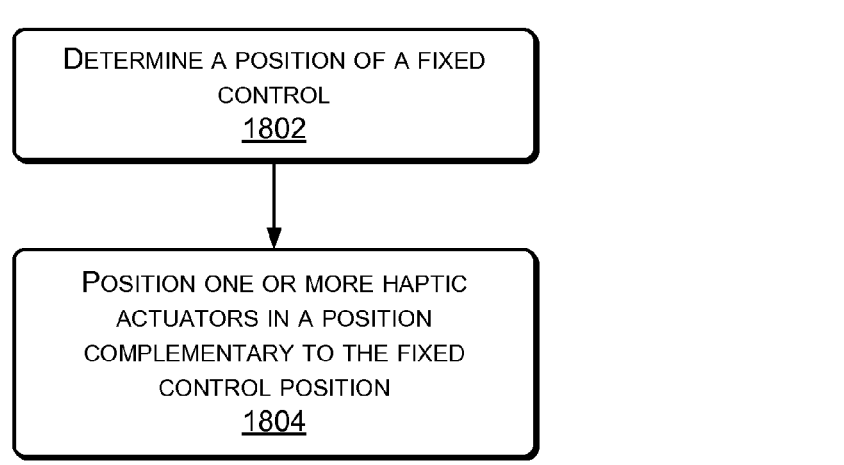
FIG. 18 is an illustrative process of positioning one or more haptic actuators adjacent to a fixed control on a device.

FIG. 18 is an illustrative process 1800 of positioning one or more haptic actuators adjacent to a fixed control on a device. At 1802, a position of a fixed control such as a button, switch, and so forth is determined. At 1804, one or more haptic actuators are positioned complementary to the fixed control position. For example, the one or more haptic actuators may be positioned within the haptic device 110 such that when the multifunction stack 104 is assembled, the one or more haptic actuators are below the fixed control position. As above, in other implementations, discrete haptic actuators or haptic actuators integrated with other components may also be used. For example, a haptic actuator separate from the haptic array may be coupled to the fixed control to provide haptic output. In another example, the haptic actuators may be integrated into the exterior 102 enclosure.

Pressure Management within the Touch Sensor

Figure 19:
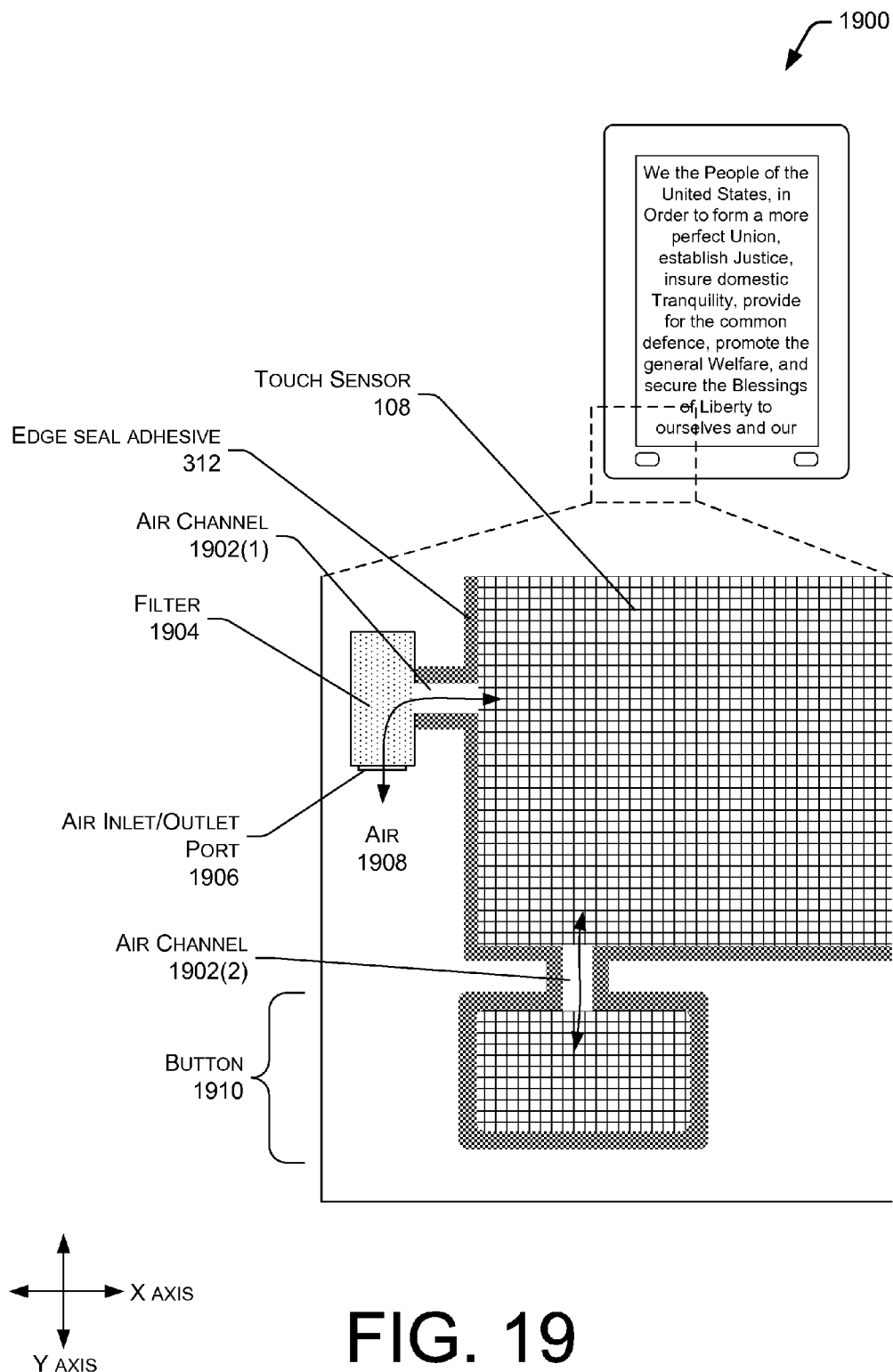
FIG. 19 is an illustrative plan view of a portion of the touch sensor configured to provide a dedicated button, as well as an air channel coupling the dedicated button to a main body of the touch sensor and a filter configured to allow an exchange of ambient air between the interior of the touch sensor and the surrounding atmosphere.

FIG. 19 is an illustrative plan view 1900 of a portion of the touch sensor 108 configured to provide a dedicated button. Within the device 100, a portion of the touch sensor 108 may be extended or added to provide for discrete fixed controls, such as buttons, sliders, and so forth. These controls may be used as a power button, to change pages of an eBook, and so forth.

Where the touch sensor 108 comprises an IFSR array, the small gap 402 as described above with regards to FIG. 4 may be present between the first touch sensor layer 216 and the second touch sensor layer 218. When an incident force is applied to the touch sensor 108, such as from a user finger, the gasses which are present within the gap may be compressed and displaced. When a volume of the touch sensor 108 is constrained, such as when the entire touch sensor is sealed, unwanted effects such as pillowing or blowout may result. Furthermore, varying ambient pressures may adversely affect a sealed touch sensor 108. For example, the low pressure on an airplane may cause the touch sensor to balloon while high pressure within a diving bell may cause the touch sensor 108 to collapse.

An air channel 1902(1) is configured to couple an interior volume of the touch sensor 108 to a filter 1904. The filter has an air inlet/outlet port 1906 and may be configured such that moisture, dust, and other contaminants are removed from air 1908 before entering the touch sensor's interior volume. The air 1908 may communicate via the filter 1904 between the outside ambient atmosphere and the touch sensor interior volume.

In a small touch sensor array, such as a discrete button 1910, upon application of an incident force the gas constrained within the volume of the touch sensor may experience compression and further distribute at least a portion of the applied force to the sides of the touch sensor volume. In other words, pressing the touch sensor button may result in "pillowing" or a similar effect. Pillowing may damage the touch array, such as by forcing the edge seal apart, and so forth. An air channel 1902(2) couples the touch sensor interior volume of the button 1910 to the interior volume of the larger touch sensor, other buttons, to the filter 1904, or to a combination thereof. Thus, when the button 1910 is pressed, the gas within the touch sensor is no longer constrained to the comparatively small interior volume of the button 1910.

Grounding Channel

Figure 20:
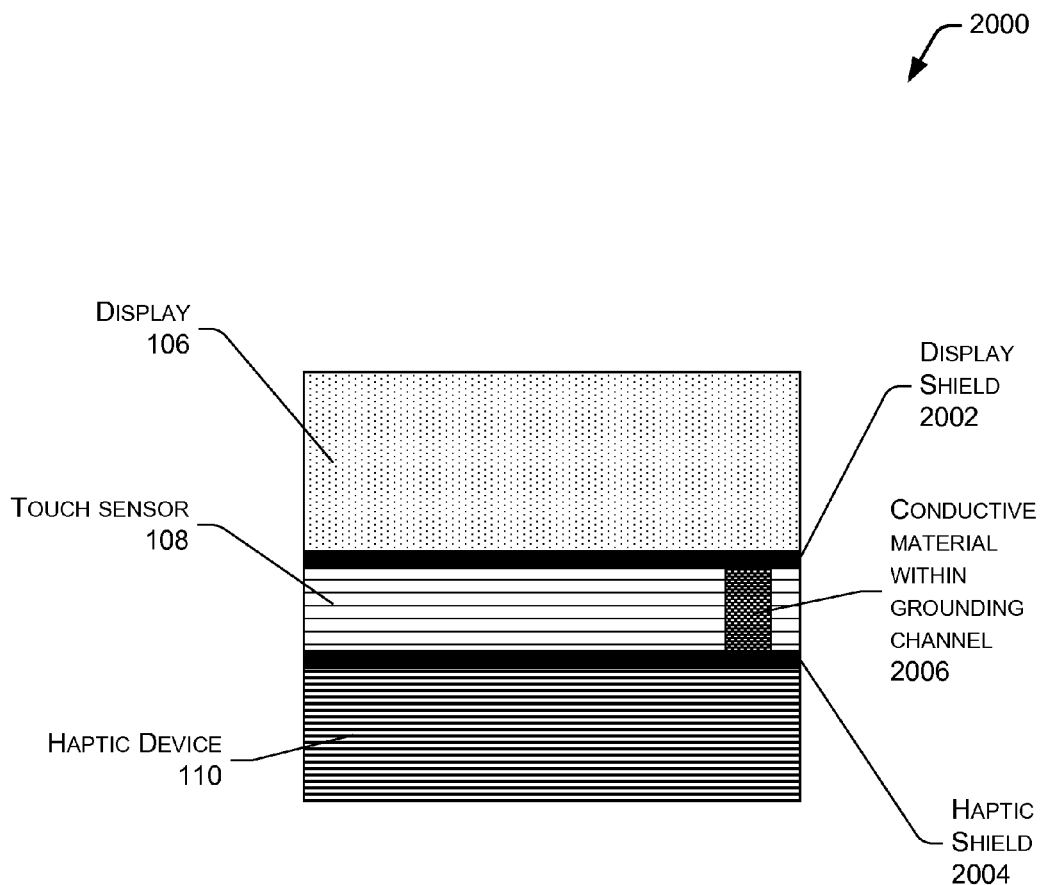
FIG. 20 illustrates a cross section of the multifunction stackup with a conductive material passing through the touch sensor layer to provide a grounding path between a display shield and a haptic shield.

FIG. 20 illustrates a cross section 2000 of the multifunction stackup 104 and a grounding channel. Given the proximity of different components such as the display 106, touch sensor 108, and the haptic device 110 in a small physical volume, electrical interference between the components may occur. Electrical shields, such as a flooded copper plane, may be coupled to an electrical ground within the device to minimize or eliminate this interference.

A display shield 2002 may be coupled to, or part of, the display 106. A haptic shield 2004 may also be present and coupled to, or part of, the haptic device 110, such as the copper flood layer 702. Within the multifunction stackup 104, the touch sensor 108 is disposed between these two shields. Inadequate coupling between the display shield 2002 and the haptic shield 2004 may adversely affect their shielding performance.

To provide adequate coupling, a grounding channel 2006 filled with a conductive material provides an electrical connection between these two shields. The grounding channel may comprise a hole, slot, or other passage allowing a conductive material to contact both shields and establish a connection. The conductive material may comprise a solid conductive slug, a conductive spring, a conductive polymer, conductive paste, and so forth.

The grounding channel 2006 may be placed so that it passes through an intervening component, such as the touch sensor 108, either through a shield of that component or through a non-conductive area. In some implementations a plurality of grounding channels 2006 may be used.

Figure 21:
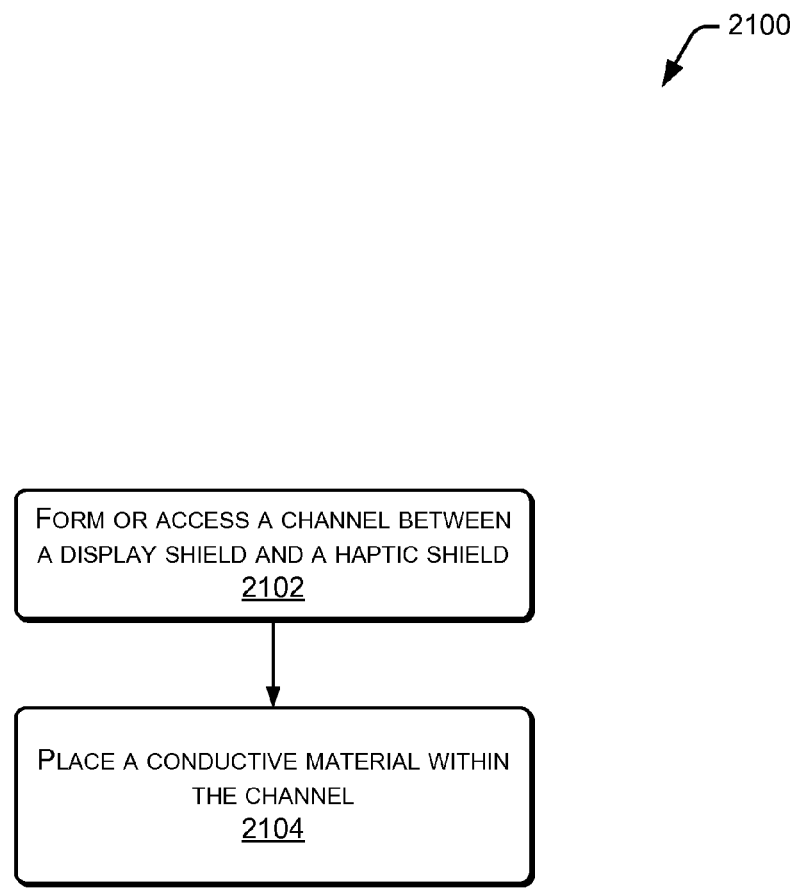
FIG. 21 is an illustrative process of grounding a display shield and a haptic shield.

FIG. 21 is an illustrative process 2100 of grounding the display shield 2002 and the haptic shield 2004. At 2102, a channel between the display shield 2002 and the haptic shield 2004 is formed or accessed through an intervening component such as the touch sensor 108. For example, the channel may be formed by drilling a hole or cutting a notch in the intervening touch sensor 108.

At 2104, a conductive material is placed within the channel 2006 such that it establishes an electrical pathway between at least the display shield 2002 and the haptic shield 2004. In other implementations, the grounding channel 2006 may electrically couple other shields or ground planes within the device. The conductive material may comprise a solid conductive slug, a conductive spring, a conductive polymer, a conductive paste, and so forth.

Maintain a Profile of the Multifunction Stackup

Following assembly, flexible structures such as the multifunction stackup 104 may not be as planar as desired. Small ripples or curves may be introduced during lamination of components within the structure, dissimilar coefficients of expansion, and so forth. Such variations in planarity are distracting to a user and are undesirable. In some situations, lack of planarity may also affect operation of the devices within the flexible structure. For example, a ripple in a touch sensor may generate an anomalous touch sensor reading.

FIG. 22 is an illustrative plan view 2200 of selected portions of the device including a frame to which the flexible structure such as the multifunction stackup 104 shown here is affixed to maintain planarity. A frame 2202 is disposed around the multifunction stackup 104. A gap 2204 is present between the frame 2202 and the multifunction stackup 104. Attachment members 2206 secure the multifunction stackup 104 to the frame 2202 under some tension. This tension pulls the multifunction stackup 104 into a planar configuration. The attachment members 2206 may comprise screws, bolts, memory metals, clips, clamps, wires, and so forth.

Figure 23:
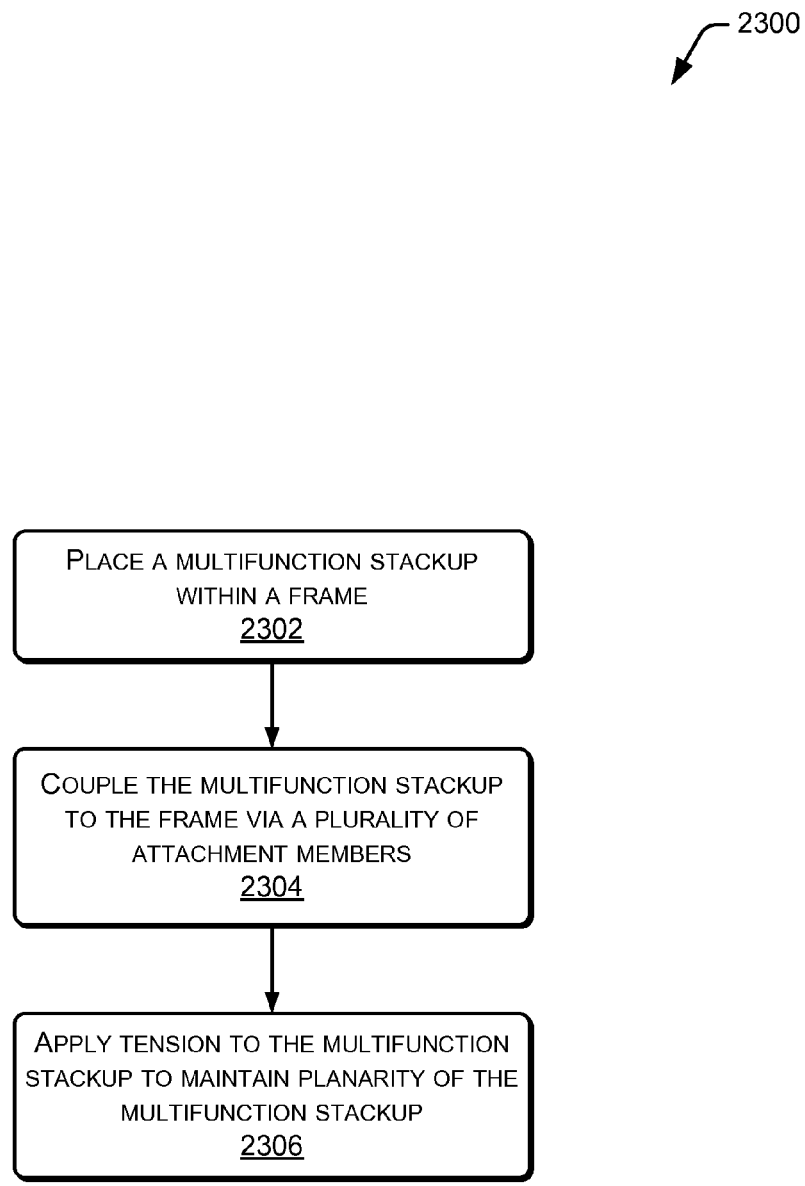
FIG. 23 is an illustrative process of maintaining planarity of the multifunction stackup by applying tension.

FIG. 23 is an illustrative process 2300 of maintaining planarity of the flexible structure such as the multifunction stackup 104 by applying tension thereto. At 2302, the multifunction stackup 104 is placed within the frame 2202. At 2304, the multifunction stackup 104 is coupled to the frame 2202 via a plurality of attachment members 2206. At 2306, tension is applied to the multifunction stackup 104 via the attachment members 2206. This tension pulls on the multifunction stackup 104 and draws it into a planar configuration.

Figure 24:
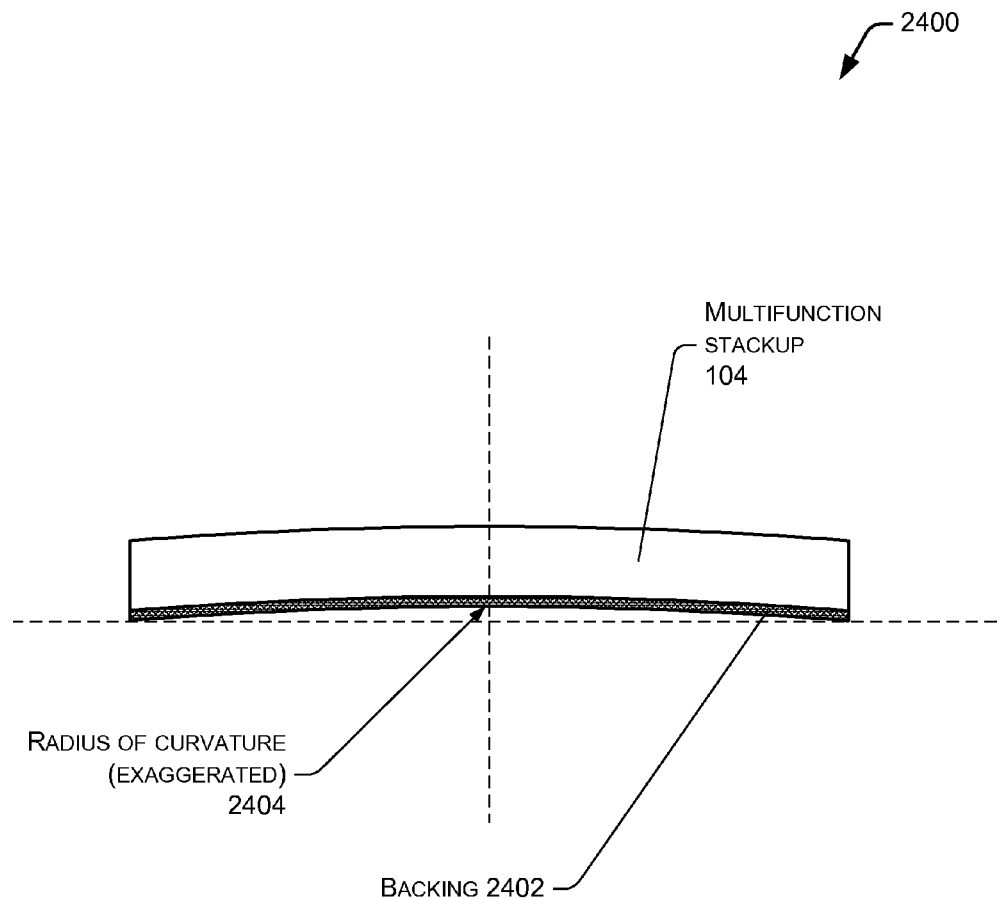
FIG. 24 is an illustrative cross section of a backing with a slight radius of curvature in a single plane to which the multifunction stackup is affixed.

FIG. 24 is an illustrative cross section 2400 of another technique to present a uniform flexible structure surface, such as the multifunction stackup 104, to the user. As shown in this illustration, a backing 2402 having a slight radius of curvature 2404 in a single plane is present. The flexible structure such as the multifunction stackup 104 is affixed to the backing 2402. In some implementations the multifunction stackup 104 is under some tension from the backing 2402.

This arrangement maintains the multifunction stackup 104 such that when pressed by the user, no voids or empty spaces resulting in "puffiness" are present. This also exploits the phenomenon in which users find a surface with a single continuous curve preferable over a surface with multiple curves, such as with rippling.

Figure 25:
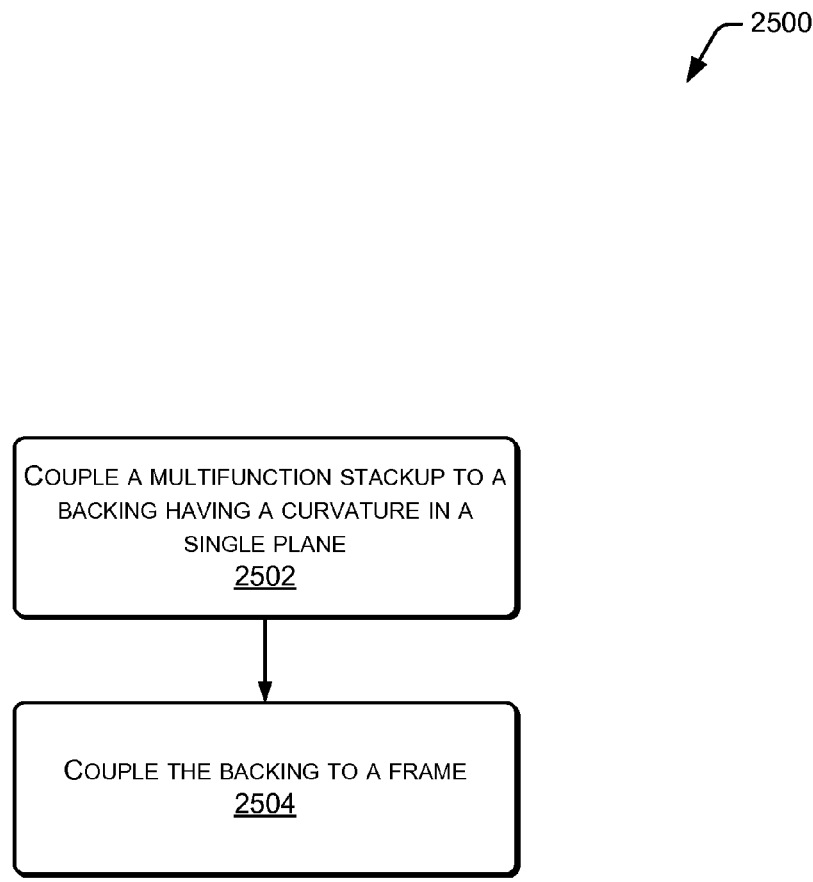
FIG. 25 is an illustrative process of maintaining tactile firmness of the multifunction stackup by affixing the multifunction stackup to a curved backing.

FIG. 25 is an illustrative process 2500 of maintaining tactile firmness of the flexible structure such as the multifunction stackup 104 by affixing the multifunction stackup to a curved backing 2402. At 2502, a multifunction stackup 104 is coupled to a backing 2402 having a curvature in a single plane.

In some implementations the various components of the flexible structure, such as the first integrated package 112 and the second integrated package 114 in the multifunction stackup 104 may be arranged into the curved configuration prior to completion of lamination. Once lamination is complete the curvature is maintained without a separate backing. In other implementations, components or structures may be arranged behind the flexible structure such that, when assembled, the flexible structure is displaced into the slightly curved profile described herein.

At 2502, the backing 2402 may be coupled to a frame within the device 100. This coupling may be accomplished by way of mechanical fasteners, adhesives, welding, interference fit, and so forth.

Multi-State Haptic Output

The presence of multiple haptic actuators in proximity to one another, such as within the high resolution haptic array 1602 allows for the generation of various haptic output effects. These output effects are further enhanced by utilizing the multiple states of contraction and expansion afforded by mutamorphic materials in the haptic actuators.

Figure 26:
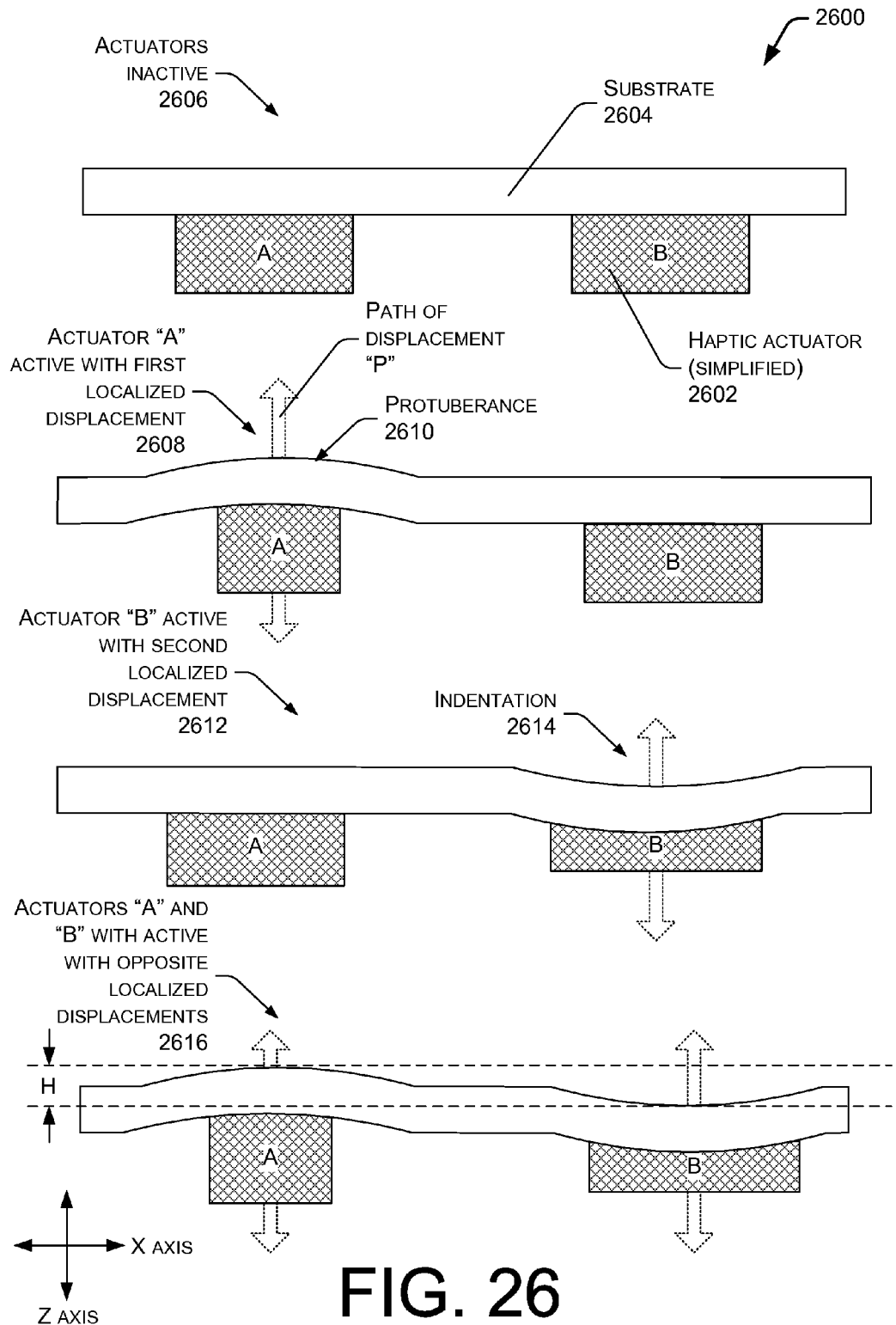
FIG. 26 is an illustrative cross section of a haptic device having two haptic actuators with opposite displacements to form enhanced tactile feedback.

FIG. 26 is an illustrative cross section 2600 of a haptic device having two actuators in various states. In this diagram, two simplified representations of haptic actuators 2602 "A" and "B" are shown on the left and right sides of the illustration, respectively, and affixed to the same side of a substrate 2604 such as the core board 704. In some implementations, one or more of the haptic actuators 2602 may be at least partially embedded within the substrate 2604. Additional layers, such as a spacer 720, display 106, touch sensor layers 216 and 218, and so forth are omitted for clarity. In some implementations the substrate 2604 may comprise FR4, metal, plastic, and so forth.

Situation 2606 shows both actuators in an inactive state. The substrate 2604 is relatively planar and un-deformed. In contrast, situation 2608 shows actuator "A" active with a first localized displacement while actuator "B" is inactive. In this situation, a localized displacement in the form of a protuberance 2610 is formed on the top surface of the substrate 2604. When the displacement exceeds a predetermined threshold of perceptible feature size, motion, and so forth, the user feels a "bump." The displacement is localized in that it affects a portion of the substrate 2604, such as the core board 702, to which the haptic actuator is coupled.

As shown here the path of displacement "P" is generally linear, that is, the majority of the displacement motion moves at least a portion of the mass, such as the core board 704, in a straight or non-arcuate path. This displacement motion is in contrast to, for example, a rotary haptic output device utilizing an eccentrically-centered mass on a rotary motor.

Situation 2612 illustrates actuator "A" as inactive while actuator "B" is active with a second localized displacement 2612. This second localized displacement 2612 has resulted in an indentation 2614 or dimple on the substrate 2604. Thus, the user may feel a "dip."

The first and second displacements may result from altering the polarity of a signal which the haptic actuators 2602 are driven. In another implementation the mutamorphic material 708 within specified haptic actuators 2602 may be varied to provide for different displacements.

Situation 2616 shows when actuators "A" and "B" are operated with displacements opposite one another. As a result of these opposing displacements, a pronounced ridge is formed extending from the top of the protuberance 2610 to the bottom of the indentation 2614, resulting in a height differential of "H". This ridge provides enhanced tactile feedback, generating a significant displacement in the substrate 2604 which is perceptible to the user. For example, such a ridge may be used to indicate the boundaries of controls presented on the display 106.

The actuators 2602 may be operated either contemporaneously, or in timed sequence (for example one after another). For example, a sequence of activation may result in ripples or the feeling of apparent motion.

In other implementations other actuator activation patterns may be used. By combining several actuators, such as within the high resolution haptic array 1600 as described in FIG. 16, various surface features and effects may be accomplished. For example, actuators 2602 may be activated with alternating displacements to produce surface textures.

Figure 27:
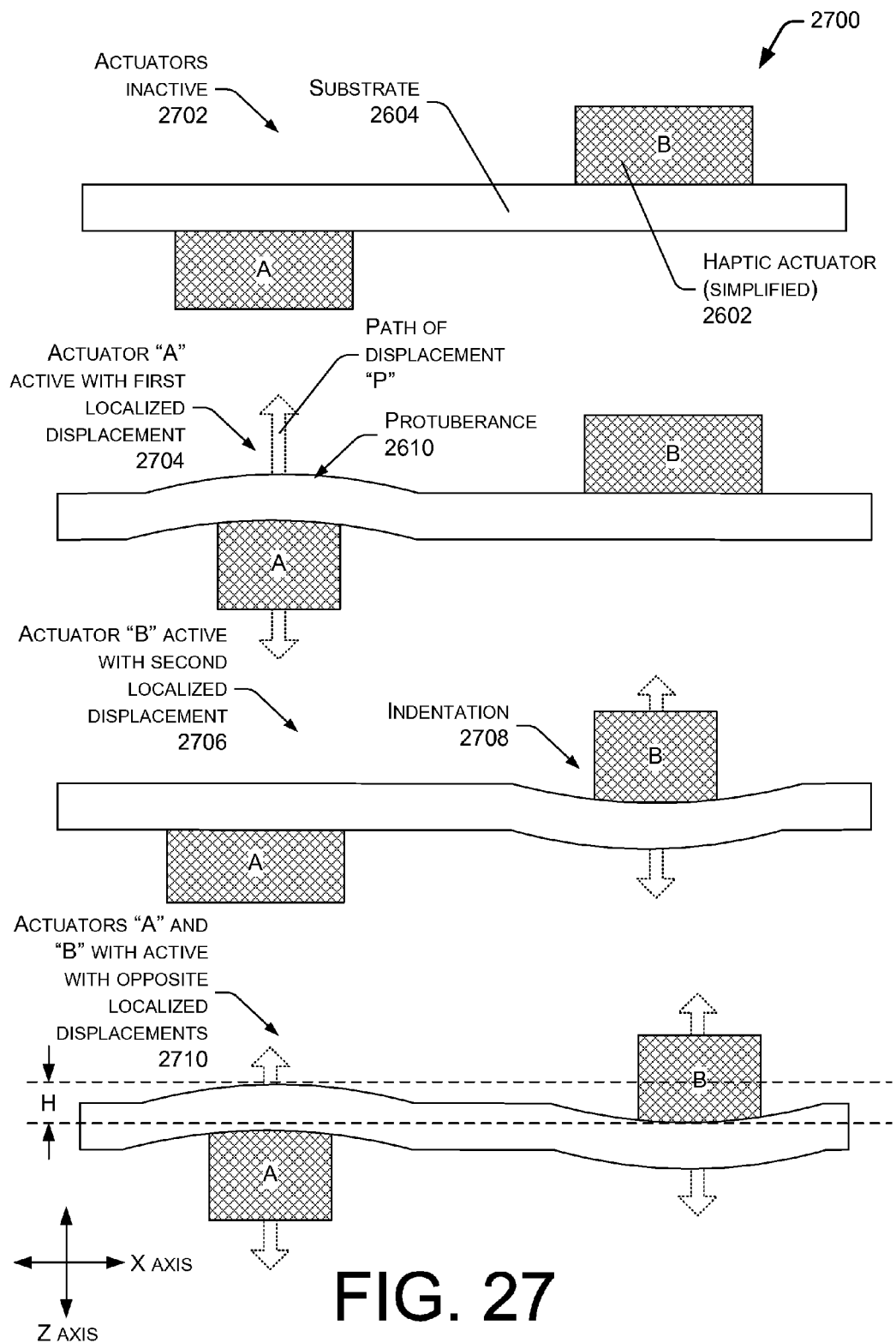
FIG. 27 is an illustrative cross section of a haptic device having two haptic actuators on opposing sides of a substrate to form enhanced tactile feedback.

FIG. 27 is an illustrative cross section 2700 of a haptic device having two haptic actuators disposed on opposing sides of the substrate 2604 and configured to create opposing displacements to form enhanced tactile feedback. As above, in this diagram, two simplified representations of haptic actuators 2602 "A" and "B" are shown on the left and right sides of the illustration, respectively, and affixed to opposing sides of the substrate 2604. As shown above, in some implementations, one or more of the haptic actuators 2602 may be at least partially embedded within the substrate 2604. Also as shown above, additional layers are omitted for clarity.

Situation 2702 shows both actuators in an inactive state. The substrate 2604 is relatively planar and un-deformed. Although not shown for clarity, a spacer or other structure coupled to the substrate 2604 would also be relatively planar and un-deformed.

Situation 2704 shows actuator "A" active with a first localized displacement while actuator "B" is inactive. In this situation, a localized displacement in the form of the protuberance 2610 is formed on the top surface of the substrate 2604.

Situation 2706 illustrates actuator "A" as inactive while actuator "B" is active with a second localized displacement resulting in an indentation 2708 with the actuator "B" therein. This indentation would thus affect overlying layers, such as the spacer or another component. In some implementations, a surface feature may be generated on layers above the substrate 2604 which resembles a ring-shaped depression corresponding to the indentation and a central peak or bump in the middle of the ring-shaped depression corresponding to the slight upward expansion of the haptic actuator "B" 2602.

As mentioned above, the first and second displacements may result from altering the polarity of a signal driving the haptic actuators 2602. In another implementation, the mutamorphic material 708 within specified haptic actuators 2602 may be varied to provide for different displacements.

Situation 2710 shows when actuators "A" and "B" are operated with displacements opposite one another. As a result these displacements, a pronounced ridge is formed extending from the top of the protuberance 2610 to the bottom of the indentation 2708, resulting in a height differential of "H". As described above, the haptic actuators 2602 may be operated either contemporaneously or in a timed sequence (for example one after another). In other implementations the haptic actuators 2602 on opposite sides of the substrate 2604 may be operated such that they generate displacement in the same direction. Also as described above, in other implementations other actuator activation patterns may be used.

Figure 28:
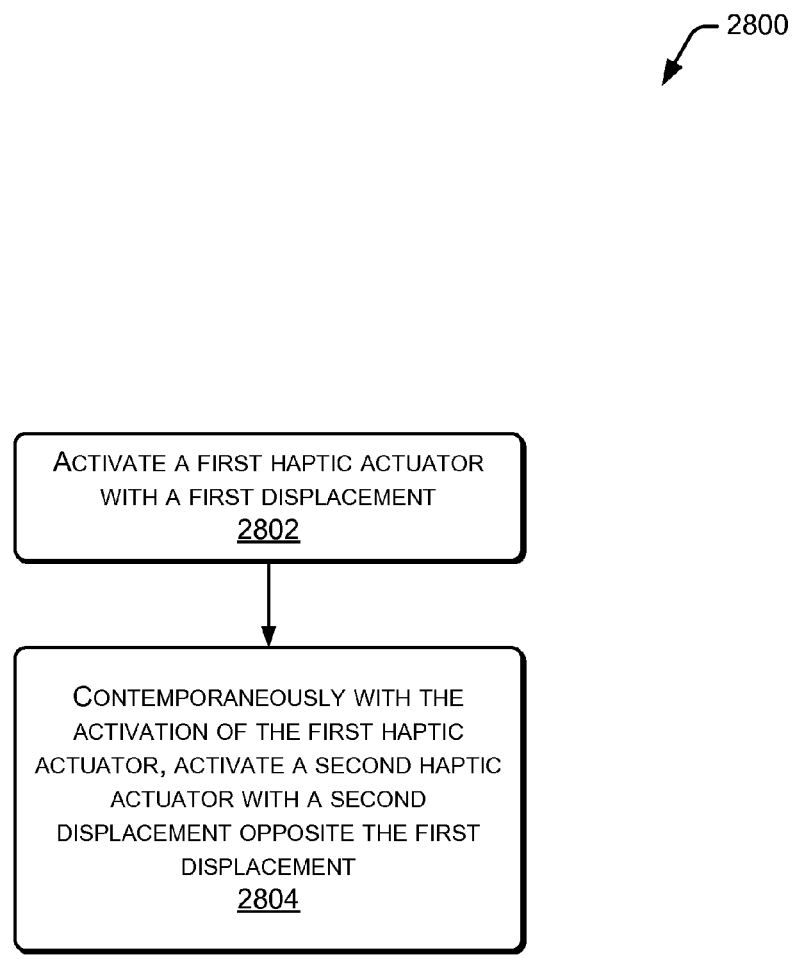
FIG. 28 is an illustrative process of generating enhanced tactile feedback by firing two or more haptic actuators with different displacements.

FIG. 28 is an illustrative process 2800 of generating fine haptic output by firing two or more haptic actuators with different displacements. At 2802, a first haptic actuator is activated with a first displacement. For example, a protuberance 2610 of the substrate may be formed. At 2804, contemporaneously with the activation of the first haptic actuator, a second haptic actuator is activated with a second displacement opposite the first displacement. This generates a pronounced surface feature which extends from the top of the protuberance to the bottom of an indentation. In some implementations the activation of the second haptic actuator may occur non-contemporaneously, such as before or after, activation of the first haptic actuator.

Haptic Actuators Embedded in Midframe

Figure 29:
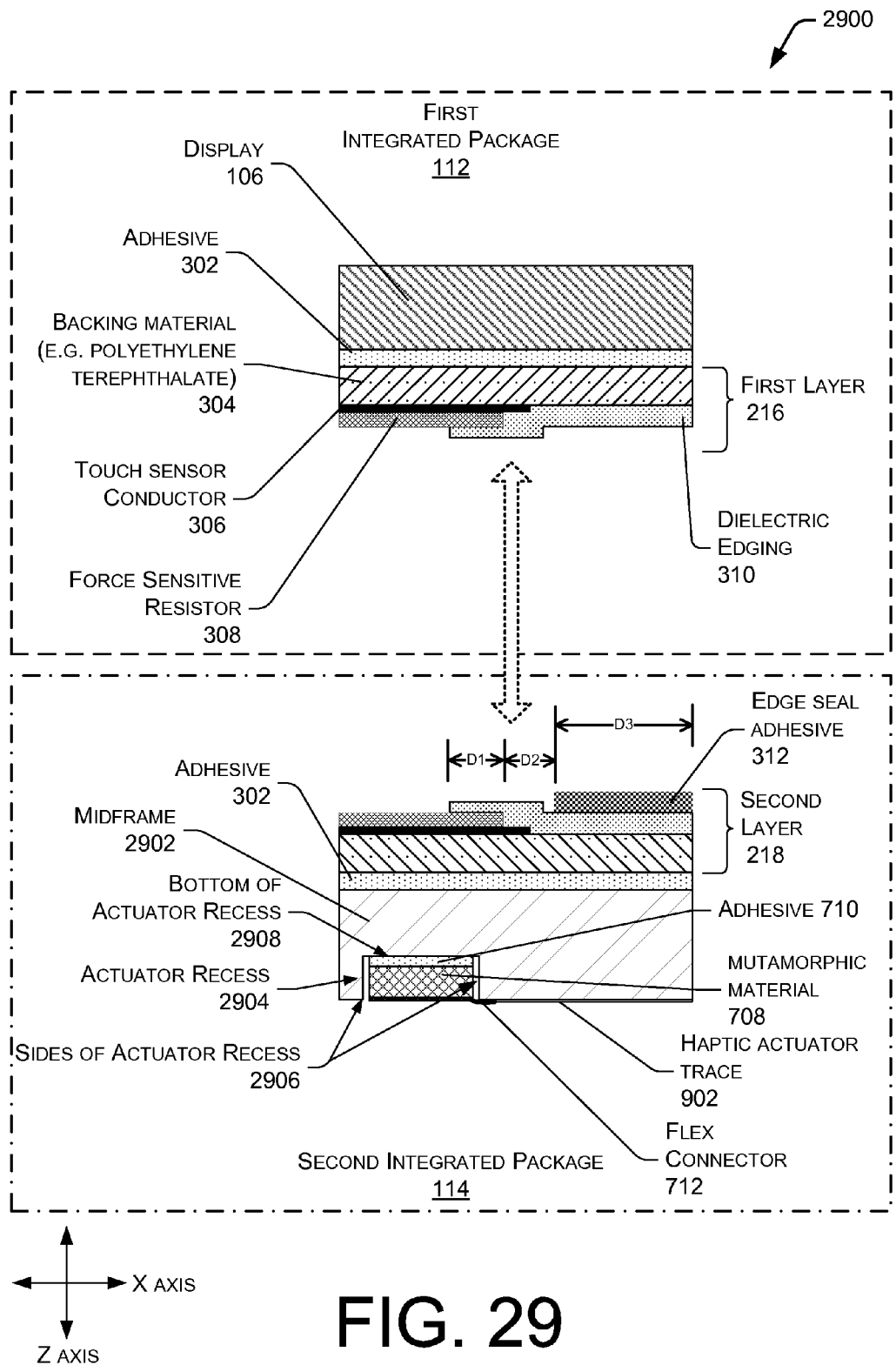
FIG. 29 illustrates a cross section of another implementation of a multifunction stackup having a haptic actuator embedded into a midframe.

FIG. 29 illustrates a cross section 2900 of another implementation of a multifunction stackup. As shown here, the haptic actuator may be embedded into a midframe, rather than emplaced on the core board 704.

The second layer 218 of the touch sensor 108 is bonded to a midframe 2902. The midframe 2902 is an internal structural element of the device 100, to which other components may be affixed. The midframe 2902 may comprise a metal, plastic, composite, and so forth.

Within the midframe 2902 an actuator recess 2904 is shown having sides 2906 and a bottom 2908. As shown here, the actuator recess 2904 is on a side of the midframe 2902 opposite the second layer 218 of the touch sensor 108. In other implementations, the actuator recess 2904 may be positioned on the same side as the second layer 218, or on both sides.

The mutamorphic material 708 is disposed at least partly within the actuator recess 2904. The mutamorphic material 708 may be directly bonded to the midframe 2902 material, or affixed via the adhesive 710. The mutamorphic material 708 may be coupled to one or more of the sides of the actuator recess 2904, instead of or in addition to being coupled to the bottom 2908 of the actuator recess.

The flex connector 712 may couple the mutamorphic material 708 to the haptic actuator trace 902, and then to the haptic controller 220. When electrically conductive, the midframe 2902 may be used to carry at least a portion of a signal from the haptic controller 220 to the mutamorphic material 708 within the actuator recess 2904.

Figure 30:
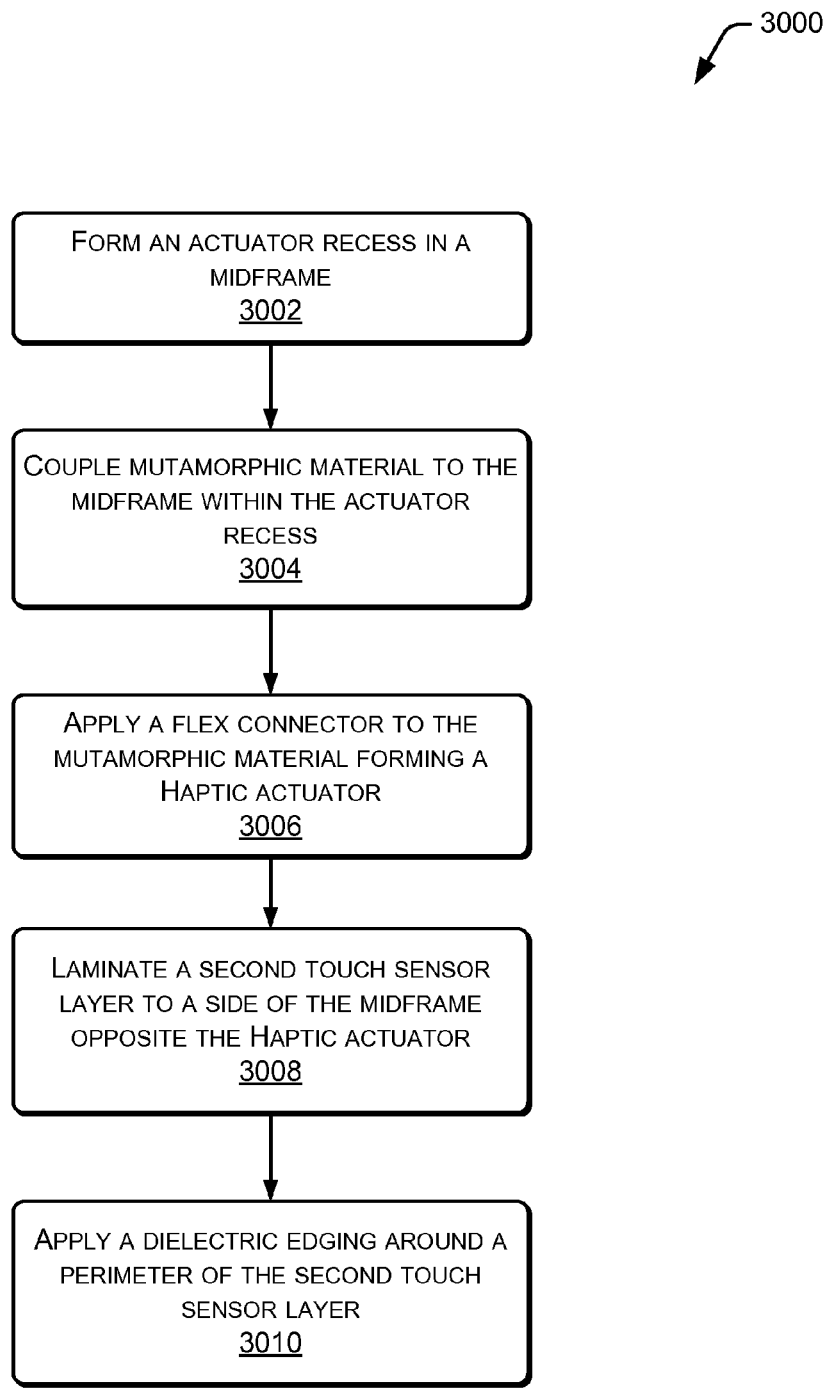
FIG. 30 is an illustrative process of assembling a portion of a multifunction stackup having a haptic actuator embedded, at least partially, within a midframe.

FIG. 30 is an illustrative process 3000 of assembling a portion of a multifunction stackup having a haptic actuator embedded, at least partially, within the midframe 2902. At 3002 the actuator recess 2904 is formed within a body of the midframe 2902. Machining, etching, photolithography, embossing, and so forth may form the actuator recess 2904.

At 3004 a haptic actuator comprising mutamorphic material 708 is coupled to midframe 2902 within the actuator recess 2904. This coupling may comprise the adhesive 710, direct deposition, baking, and so forth.

At 3006, a flex connector 712 is applied to the mutamorphic material forming a haptic actuator. At 3008 the second touch sensor layer 218 is laminated to a side of the midframe 2902 opposite the haptic actuator and associated actuator recess 2904.

At 3010, the dielectric edging 310 is applied around a perimeter of the second touch sensor layer 218. The dielectric edging 310 thus forms a ring around the touch sensor layer.

Actuator Tabs

Figure 31:
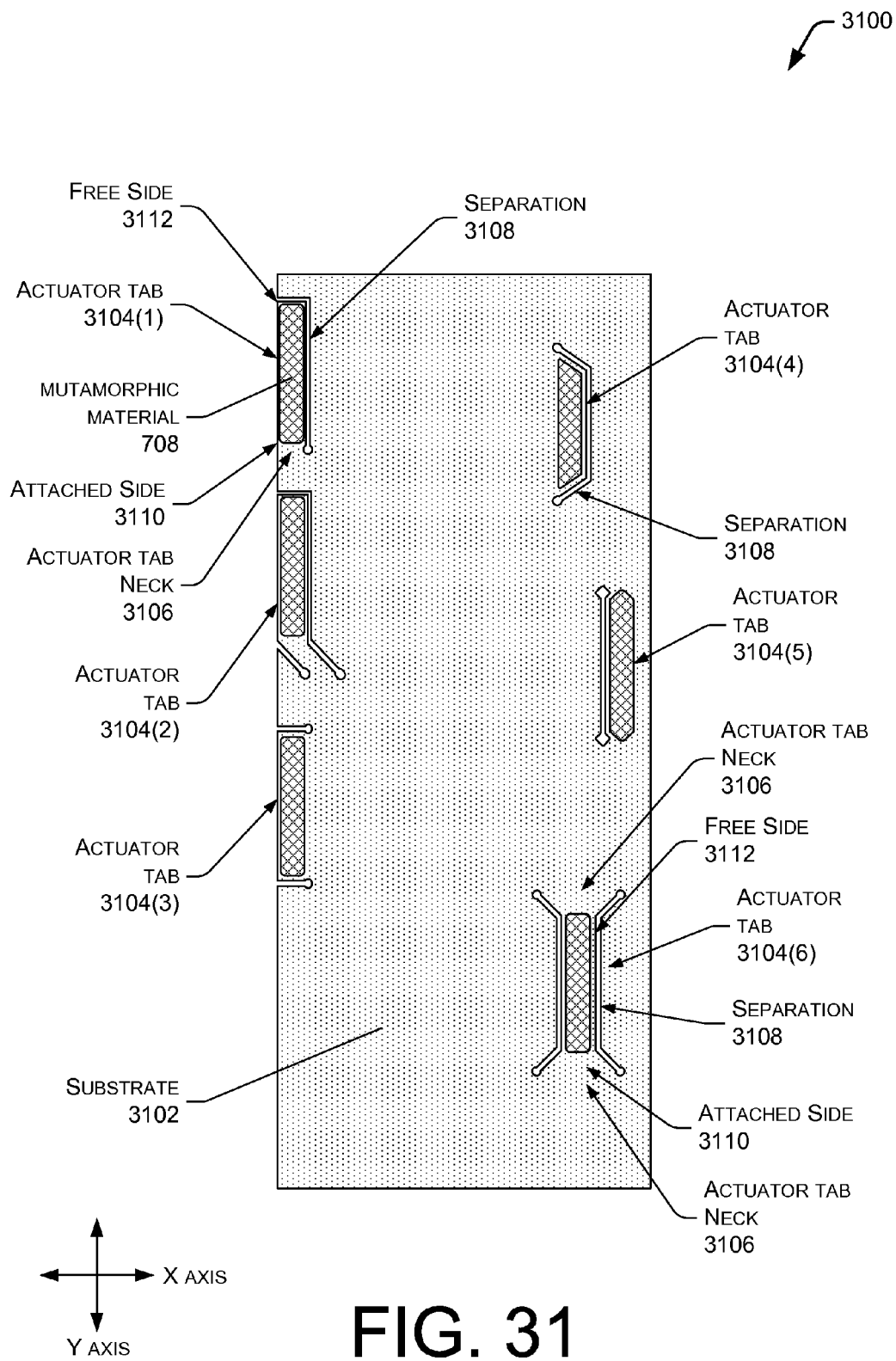
FIG. 31 illustrates a plan view of several actuator tabs incorporated into a substrate such as a display substrate.

FIG. 31 illustrates a plan view 3100 of several actuator tabs incorporated into a substrate. The substrate 3102 may be dedicated to the haptic output device, or may function as a substrate of another component. For example, the substrate 3102 may serve the function of acting as a display substrate onto which other display 106 components such as the front panel laminate are affixed.

The substrate 3102 may comprise metal, glass, plastic, or a composite configured to transfer mechanical energy from an active actuator, ultimately to the user. The substrate 3102 may also be configured to resiliently deform under the influence of the active actuator.

An actuator tab 3104(1) is depicted which connected to the substrate 3102 via an actuator tab neck 3106 on at least one side of the actuator tab 3104(1). At least one separation 3108 permits at least a portion of the actuator tab 3104(1) to move relative to the substrate 3102. This separation may be a lance or cut in the substrate 3102, a cutout such as from a punch, and so forth. The mutamorphic material 708 is coupled to the actuator tab 3104(1), and is configured to, when activated, generate a deformation of at least a portion of the actuator tab 3104. This deformation, in turn, results in motion that may result in a physical displacement of the substrate 3102.

The actuator tab 3104 may be formed from a contiguous portion of the substrate 3102. In other implementations, the actuator tab 3104 may be a separate piece that is joined to the substrate 3102. This joining may comprise bonding, welding, compression, mechanical fasteners, and so forth.

The actuator tab 3104(1) may have one or more attached sides 3110 which are proximate to the actuator tab neck 3106. The actuator tab 3104(1) also has at least one free side 3112 that is separated from a body of the substrate 3102, such as depicted by the separation 3108. The actuator tab 3104 and mutamorphic material 708 form a haptic actuator.

A flex connector 712 may form at least a portion of a coupling of the haptic actuator to the haptic controller 220. For clarity of illustration, and not by way of limitation, the flex connector 712 associated with haptic actuators is omitted in this and the subsequent figures.

In some implementations, actuator tabs 3104 may have more than one attached side, and thus more than one neck. For example, actuator tab 3104(6) has been formed within the body of the substrate 3102 with two attached sides 3110 and thus has two actuator tab necks 3106.

Figure 32:
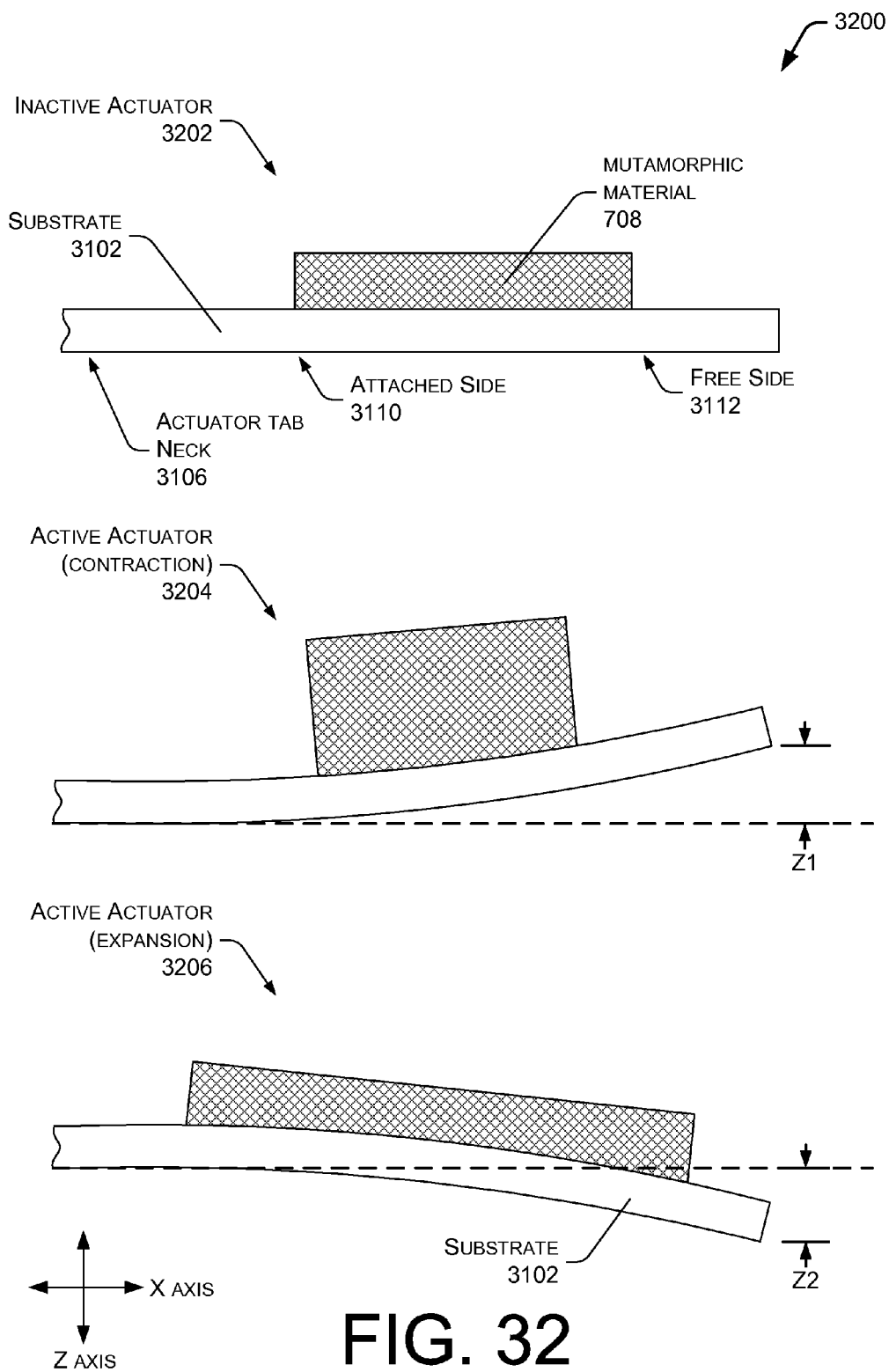
FIG. 32 illustrates a cross section of an actuator tab in several states.

FIG. 32 illustrates a cross section 3200 of a actuator tab in several states. An inactive actuator 3202 state shows the substrate 3102 is generally planar when the mutamorphic material is not active. However, in some implementations the substrate 3102 of the actuator tab 3104 may incorporate one or more curves.

An active actuator state with the mutamorphic material 708 in a contracted state 3204 is shown. In this state, the free side 3112 of the haptic actuator 3104 has been displaced upwards by a distance Z1 from the original, inactive, state. Due to the resilience of the substrate 3102, the substrate 3102 will rebound after deactivation of the mutamorphic material 708.

An actuator state with the mutamorphic material 708 in an expanded state 3206 is also shown. In this state, the free side 3112 of the haptic actuator has been deflected downwards by a distance of Z2. As above, due to the resilience of the substrate 3102, the substrate 3102 will rebound after deactivation of the mutamorphic material 708.

The movement of the actuator 3104 generates physical displacements, such as vibrations. These displacements transfer to the body of the substrate 3102 via the actuator tab neck 3106. The physical displacements propagate from the substrate 3104 to the user as haptic output.

Figure 33:
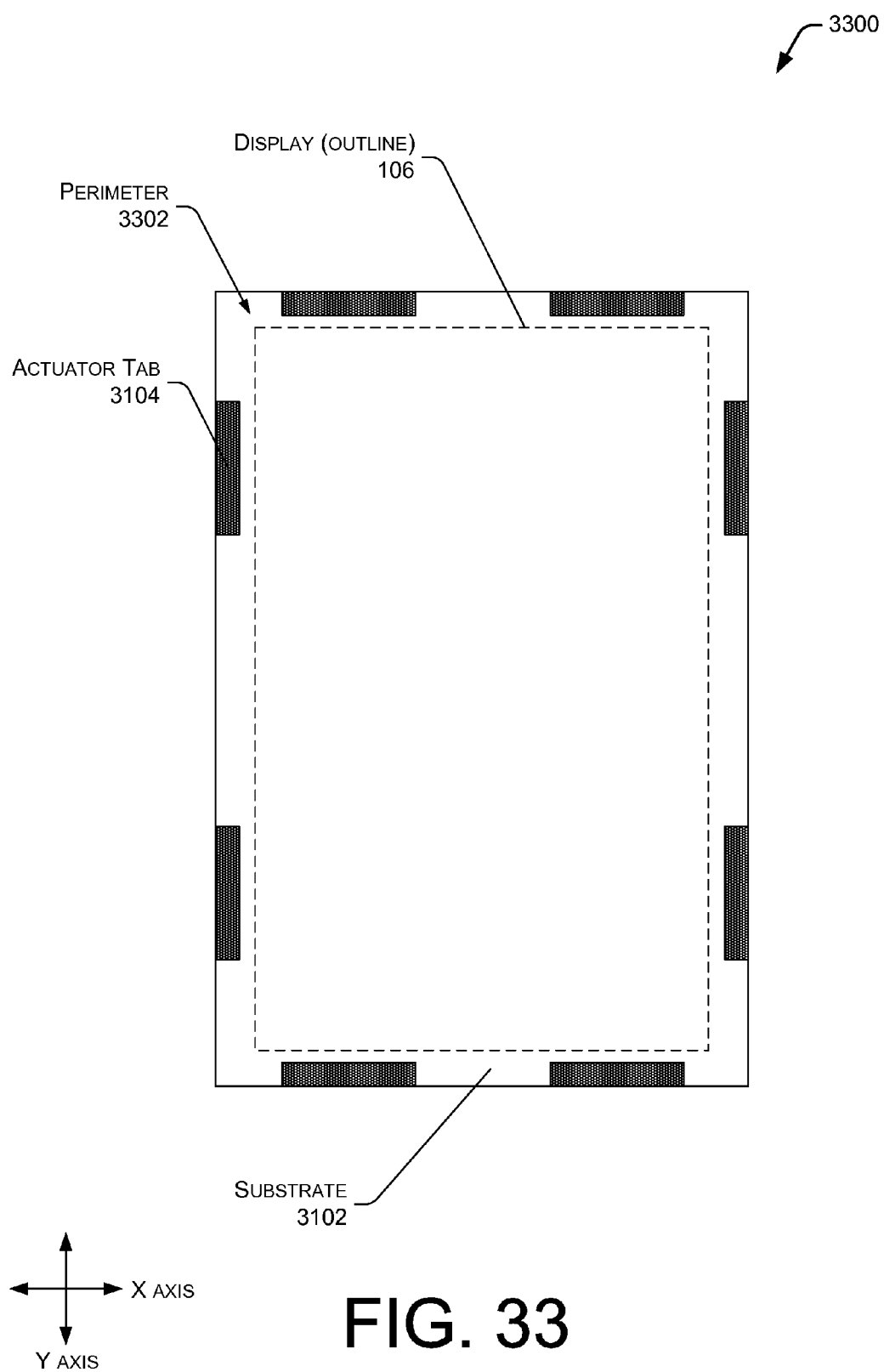
FIG. 33 illustrates a plan view of a plurality of actuator tabs distributed around a perimeter of a substrate.

FIG. 33 illustrates a plan view 3300 of a plurality of actuator tabs distributed around a perimeter of a display substrate. For reference, a broken-line outline of an active portion of the display 106 is shown. For example, where the display 106 comprises an electrophoretic display the outline as shown indicates the location of a front panel laminate containing electrophoretic slurry that generates an image. In this illustration, the substrate 3102 also acts as the substrate for the display 106, and as such may contain or be coupled to other display components such as the front panel laminate.

A plurality of actuator tabs 3104 are disposed around a perimeter 3302 of the substrate 3102 of the display 106. These actuator tabs 3104 may use one or more of the configurations as shown above with respect to FIG. 31, or configurations. For example, the actuator tabs 3104 along the top and bottom edges of the substrate 3102 may be the configuration shown at 3104(1), while the actuators tabs along the sides may be the configuration shown at 3104(6). Different actuator tab configurations may be selected based upon different forces and effects.

Figure 34:
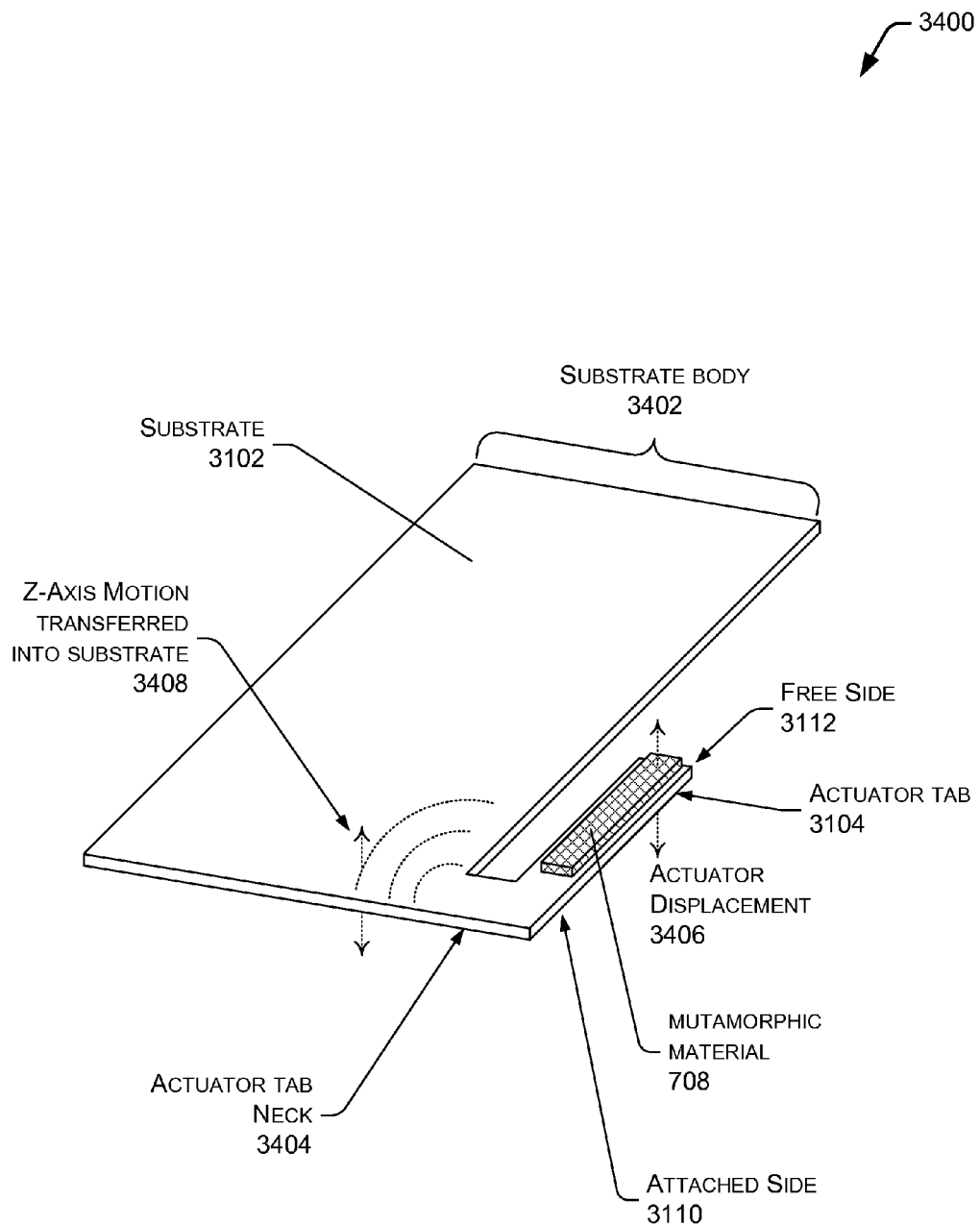
FIG. 34 is a perspective view of a substrate incorporating an actuator tab that is coplanar with the substrate.

FIG. 34 is a perspective view 3400 of a substrate incorporating an actuator tab that is coplanar with the display substrate. In the configuration shown, the actuator tab 3104 extends away from the substrate body 3402 via the actuator tab neck 3404. While a single actuator tab 3104 is shown here, in other implementations a plurality of actuators tabs may present. The actuator tab 3104 is configured to remain within the same plane as the substrate body 3402 when the mutamorphic material 708 is inactive.

When the mutamorphic material 708 is active, the actuator tab 3104 is displaced generally orthogonal to the plane of the substrate 3102, as indicated by actuator displacement arrows 3406. The physical displacement of the actuator tab 3104 results in a motion along the z-axis, which is orthogonal to the plane of the substrate 3102. This motion transfers via the actuator tab neck 3404 to the substrate 3102 and results in a z-axis motion 3408 in the substrate 3102.

Figure 35:
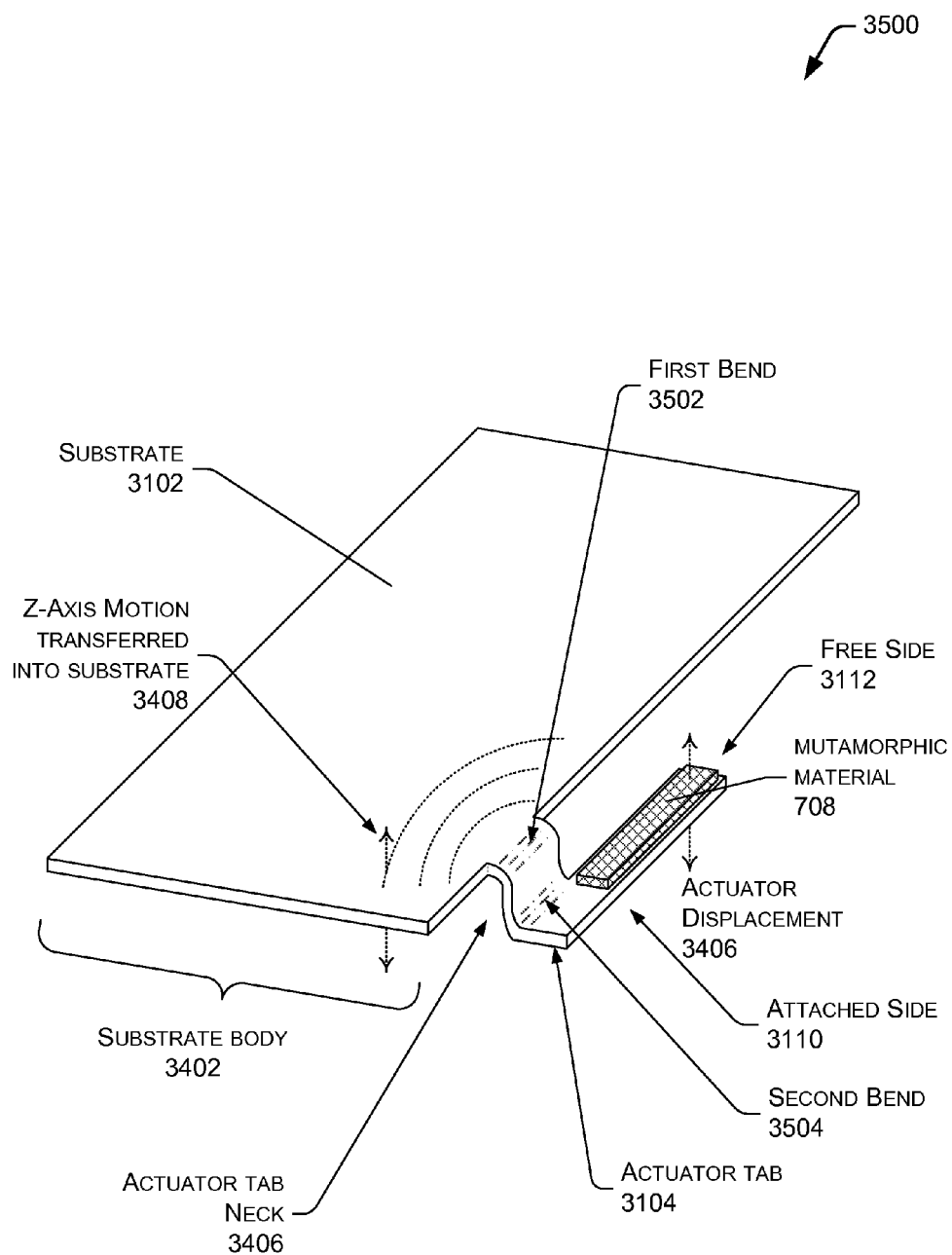
FIG. 35 is a perspective view of a substrate incorporating an actuator tab that is parallel with, but non-coplanar to, the substrate.

FIG. 35 is a perspective view 3500 of a display substrate incorporating an actuator tab that is parallel with, but non-coplanar to, the substrate. In this implementation, a first bend 3502 and a second bend 3504 are formed into the actuator tab neck 3404. These bends serve to displace the actuator tab 3104 such that a plane of the actuator tab 3104 is parallel with, but non-coplanar to, the display substrate 3102. Repositioning of the actuator tab 3104 may be used, for example, to reposition the actuator tab 3104 when internal arrangement of the device 100 may call for moving the actuator tab 3104 to a different location. As above, in other implementations additional actuator tabs 3104 may be present.

Figure 36:
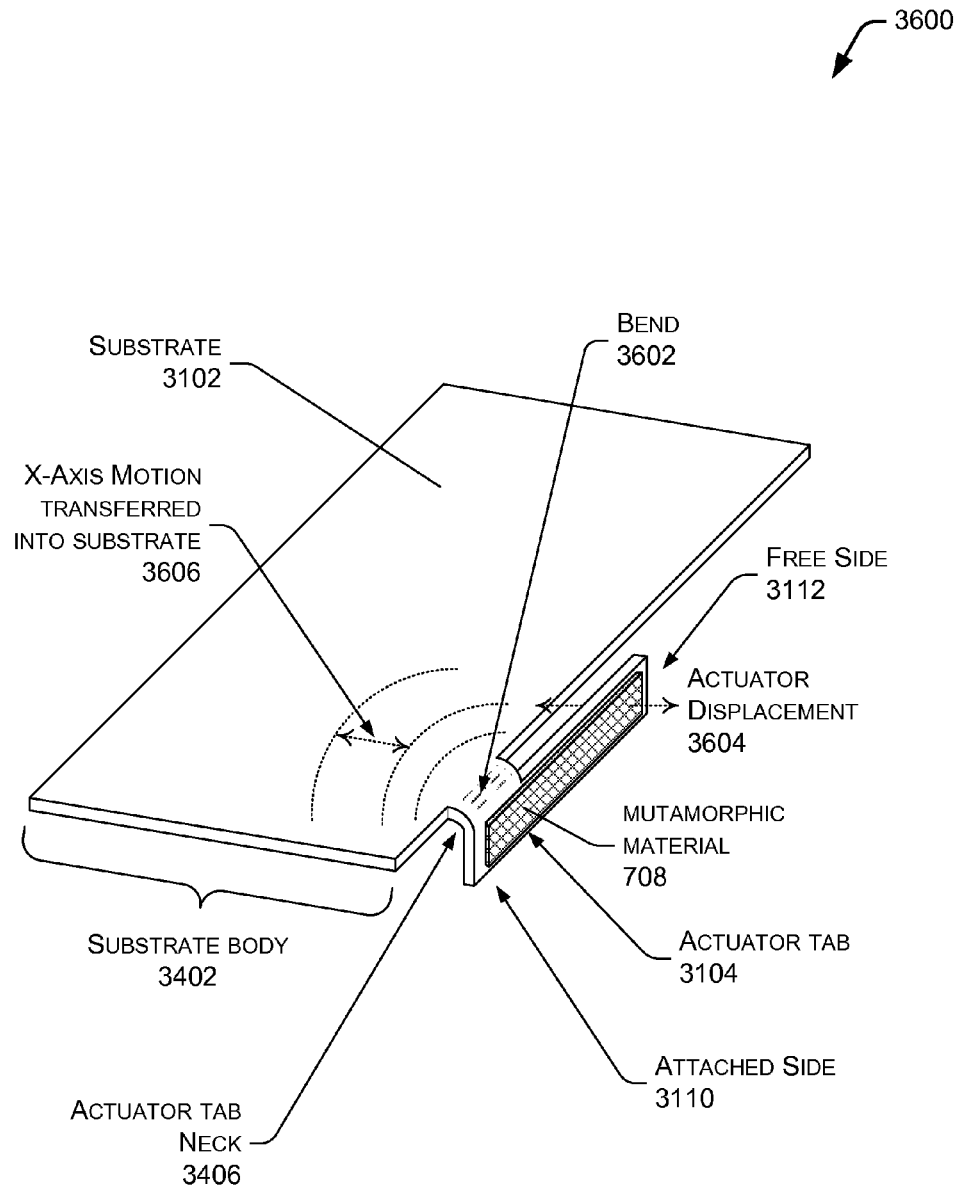
FIG. 36 is a perspective view of a substrate incorporating an actuator tab that is non-coplanar and non-parallel with the substrate.

FIG. 36 is a perspective view 3600 of another implementation of a substrate incorporating an actuator tab. As shown here, the actuator tab 3104 has been displaced due to a bend 3602 in the actuator tab neck 3404 such that the actuator tab 3104 is non-coplanar and non-parallel with the substrate body 3402. As above, in other implementations additional actuator tabs 3104 may be present.

When activated, the mutamorphic material 708 displaces at least a portion of the actuator tab 3104 generally in a direction indicated by an actuator displacement 3604 arrow. This results in a motion of the substrate body 3402 along the x-axis, that is in the plane formed by the substrate body 3402.

Haptic output which is orthogonal to the plane of the substrate body 3402 may generate output that is audible to a user. For example, physical displacement of the substrate 3102, which is orthogonal to the plane of the substrate 3102, may cause the substrate to act like a diaphragm of a speaker, producing audible output. In some implementations, this audible output may be undesirable for several reasons. This audible output may be distracting to the user, interfere with desirable audio output such as from speakers, may interfere with operation of a microphone within the device, and so forth.

Configuring the actuator tab 3104 so that the generated motion is in-plane with the substrate body 3402 and not orthogonal to the substrate body 3402 may reduce or eliminate audible output. In one implementation, the actuator tab 3104 is arranged as shown here such that the substrate body 3402 is moved generally side-to-side along the x-axis while the mutamorphic material 708 on the actuator tab 3104 is active. It is worthwhile to note that the user is still able to perceive this side-to-side motion as a haptic output.

Haptic output may thus be generated by a physical displacement of the substrate body 3402 such that the physical displacement is within a plane of the substrate body 3402 and substantially free from motion orthogonal to the plane of the body of the substrate. In some implementations, substantially free from motion orthogonal to the plan of the body of the body of the substrate may be considered when amplitude of the orthogonal motion is less than ten percent the amplitude of the in-plane motion. The substrate body 3402 is substantially free from displacement orthogonal to the plane of the substrate body when the amplitude of the physical displacement within the plane of the substrate body is greater than the amplitude of the physical displacement orthogonal to the plane of the substrate body.

For the purposes of illustration, the plane of the substrate body 3402 is the x-y plane defined by the two longest dimensions of the substrate 3402.

Figure 37:
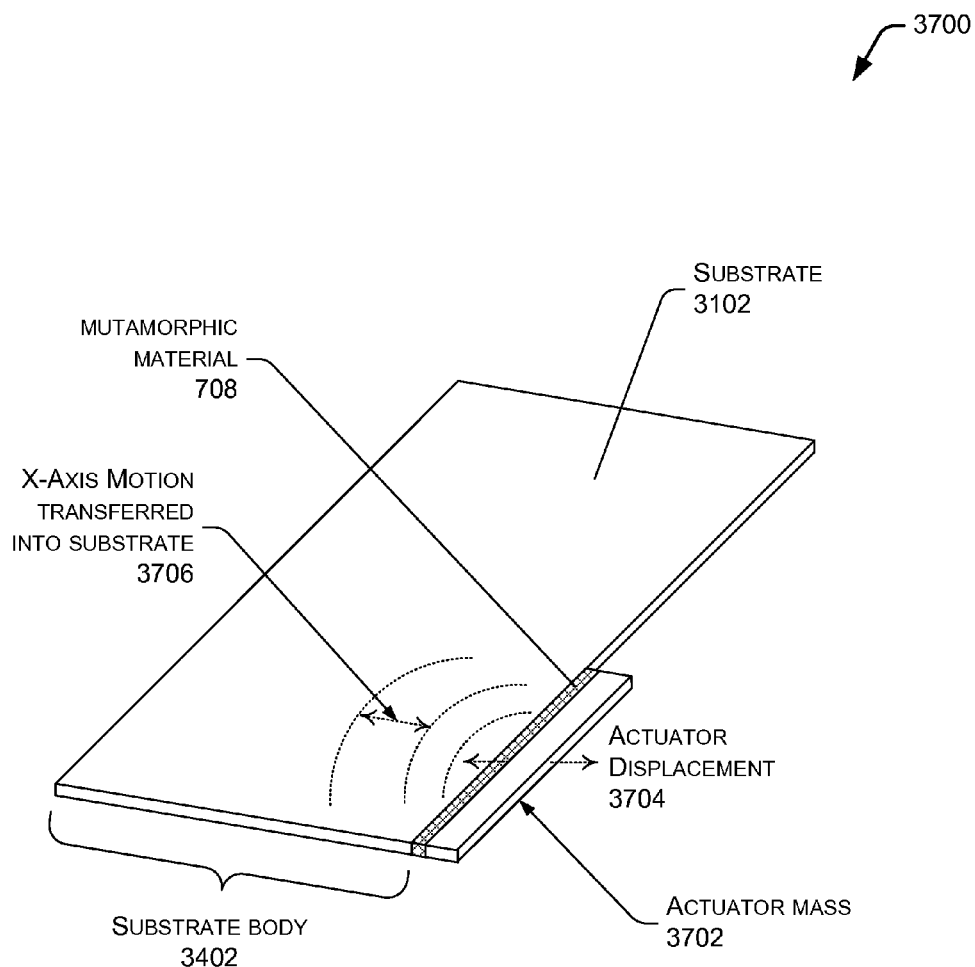
FIG. 37 is a perspective view of a substrate incorporating a mutamorphic haptic actuator configured to generate in-plane displacements of the substrate.

FIG. 37 is a perspective view 3700 of a substrate incorporating a haptic actuator configured to generate in-plane displacements of the substrate. In this arrangement, an actuator mass 3702 is coupled to the substrate body 3402 via mutamorphic material 708. When activated, the mutamorphic material 708 moves the actuator mass 3702 within the x-y plane of the substrate 3102 along a direction indicated by arrows 3704. Such motion results in an x-axis motion 3706 which is transferred into the substrate body 3402 to produce haptic output.

In some implementations the actuator mass may be another component of the device 100. For example, the actuator mass may comprise the midframe 2902, the battery 240, and so forth. In another implementation, the actuator mass may comprise the enclosure 102 or other portion of the device 100. In this implementation, the substrate 3102 and components coupled thereto, such as the display 106, touch sensor 108, and so forth may be configured to move within the x-y plane within the device. When the actuator mass 3702 and the substrate 3102 are electrically conductive, they may be used instead of flex connectors 712 to provide the electrical signal to the mutamorphic material 708.

Figure 38:
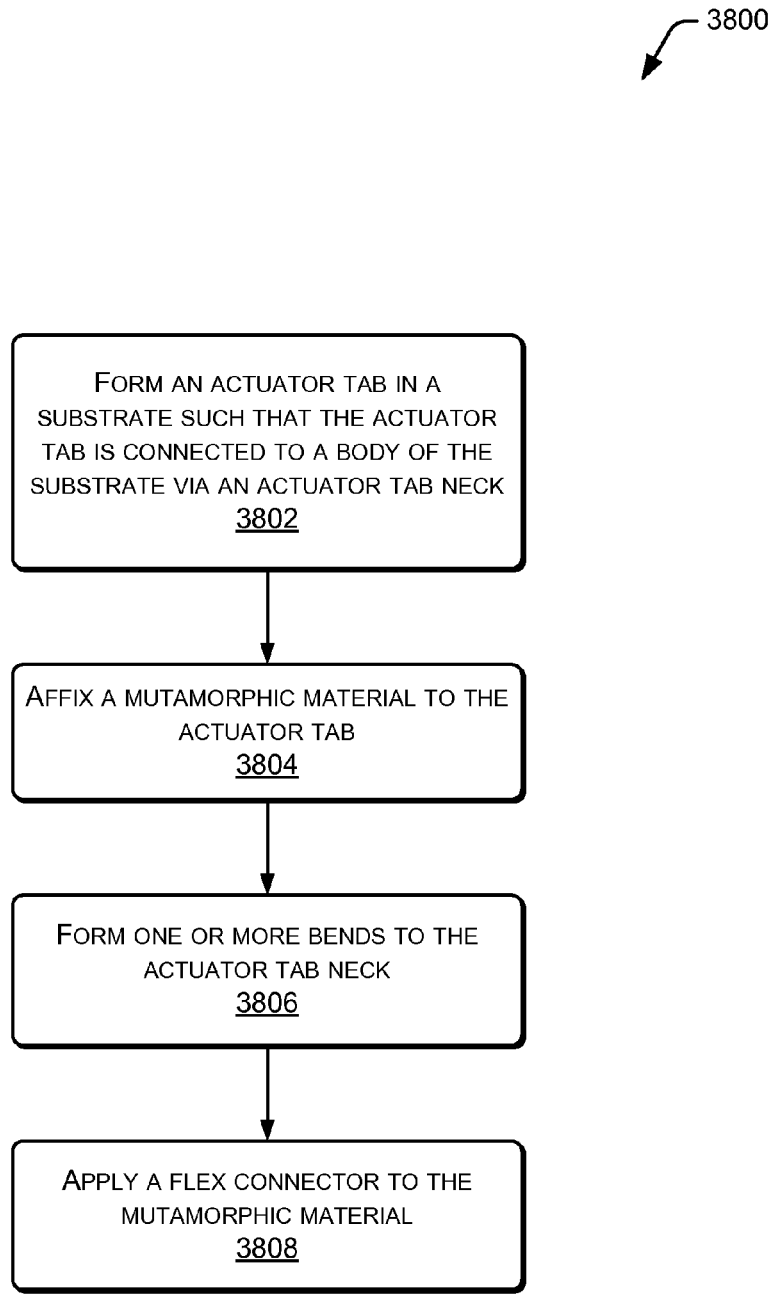
FIG. 38 is an illustrative process of forming an actuator tab.

FIG. 38 is an illustrative process 3800 of forming an actuator tab. At 3802 an actuator tab 3104 is formed in a substrate such that the actuator tab 3104 is connected with the substrate body 3402 via the actuator tab neck 3404. In one implementation the actuator tab 3104 may be lanced, punched, or otherwise formed from the substrate 3102 material itself, such that the actuator tab 3104 and the substrate 3102 are contiguous. In another implementation, the actuator tab 3104 may be separate and joined to the substrate 3102. This joining may comprise welding, bonding, and so forth.

At 3804 the mutamorphic material 708 is affixed to at least a portion of the actuator tab 3104. The affixing may comprise direct placement of the mutamorphic material upon the actuator tab 3104, adhesives, mechanical fasteners, and so forth.

At 3806, one or more bends to the actuator tab neck 3404 may be formed. These bends may be used to displace the actuator tab, such as described above with regards to FIGS. 35-36.

At 3808, one or more flex connectors 712 are applied to the mutamorphic material 708. The one or more flex connectors 712 provide an electrical pathway for a signal, such as from the haptic controller 220. This signal from the haptic controller activates the mutamorphic material 708.

Figure 39:
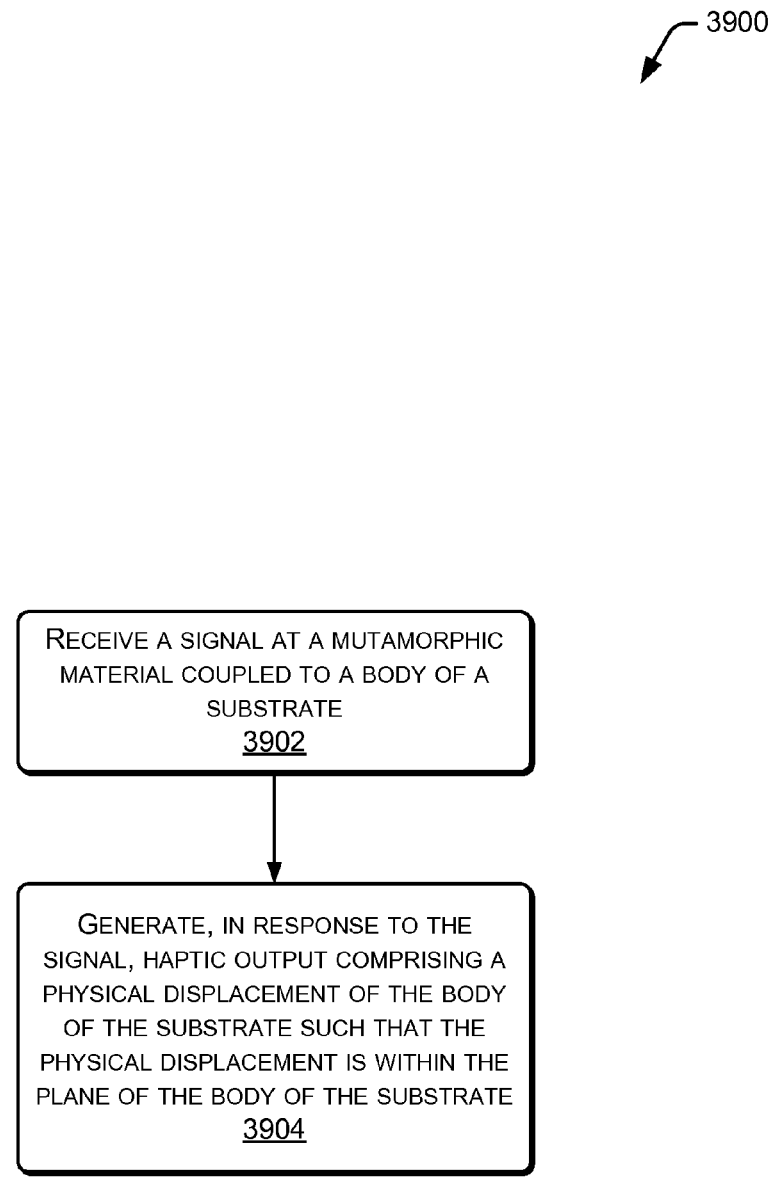
FIG. 39 is an illustrative process of generating a haptic output comprising a physical displacement of a substrate such that the motion is within the plane of the substrate.

FIG. 39 is an illustrative process 3900 of generating a haptic output comprising a physical displacement of the display substrate such that the motion is within the plane of the display substrate. This in-plane motion may reduce audible output produced by haptic output.

At 3902, a signal is received at a haptic actuator coupled to the substrate body 3402. The haptic actuator may comprise the actuator tab 3104 and mutamorphic material 708 thereon. At 3904, in response to the signal, haptic output is generated. This haptic output comprises a physical displacement of the substrate body 3402 such that the physical displacement is within the x-y plane of the substrate body 3402 and substantially free from motion orthogonal relative to the x-y plane of the body of the substrate. In other words, the motion of the substrate is predominately in the x-y plane, and not along the z-axis.

As described above, the substrate 3102 may comprise a substrate of the display 106. This in turn may be part of a multifunction stackup 104, resulting in a compact display, touch sensor, and haptic output device which is relatively easy to manufacture. By providing for the haptic output to manifest as movement in the x-y plane, the audible output from the haptic device is minimized.

Conclusion

Although the subject matter has been described in language specific to structural features and/or methodological acts, it is to be understood that the subject matter defined in the appended claims is not necessarily limited to the specific features or acts described herein. Rather, the specific features and acts are disclosed as illustrative forms of implementing the claims. For example, the methodological acts need not be performed in the order or combinations described herein, and may be performed in any combination of one or more acts.

What is claimed is:

1. A haptic output device comprising:
   a display that includes a display substrate configured to resiliently deform in response to a force generated by a haptic actuator, wherein the display substrate is below a haptic shield that is between a first component of the haptic output device and a second component of the haptic output device;
   an actuator tab formed from a portion within the display substrate such that the actuator tab remains connected to a body of the display substrate via an actuator tab neck on at least one side and separated from the body of the display substrate by at least one separation on at least one other side; and
   a mutamorphic material coupled to the actuator tab to form the haptic actuator.

2. The haptic output device of claim 1, wherein the actuator tab neck comprises one or more bends.

3. The haptic output device of claim 2, wherein the one or more bends of the actuator tab neck cause the actuator tab to be parallel with, but non-coplanar to, the display substrate.

4. The haptic output device of claim 1, wherein the actuator tab neck includes a bend such that the actuator tab is non-coplanar with the body of the display substrate.

5. The haptic output device of claim 1, wherein the actuator tab neck includes one or more bends configured such that when the haptic actuator generates the force, the force creates an in-plane displacement of the body of the display substrate.

6. The haptic output device of claim 1, wherein the display substrate comprises stainless steel.

7. The haptic output device of claim 1, further comprising a flex connector configured to couple the mutamorphic material to a haptic controller configured to generate an activating signal.

8. The haptic output device of claim 7, wherein the flex connector comprises a conductive tape proximate to the mutamorphic material, a copper conductor proximate to the conductive tape, and a polyamide carrier proximate to the copper conductor.

9. The haptic output device of claim 1, wherein the mutamorphic material comprises a ceramic.

10. The haptic output device of claim 1, wherein the surface of the display comprises a continuous surface, and wherein the actuator tab is configured to translate haptic feedback generated by the haptic actuator to a region of the surface of the display.

11. A device comprising:
a display comprising a user facing surface;
a touch sensor;
a haptic output device comprising:
    an inner substrate;
    an actuator tab connected to a body of the inner substrate via an actuator tab neck, the actuator tab being configured to move relative to the inner substrate; and
    a mutamorphic material coupled to the actuator tab; and
a haptic shield disposed between the display and the haptic output device,
wherein the touch sensor and the inner substrate are included in the device as substrates of the display located below the user facing surface of the display.

12. The device of claim 11, wherein the user facing surface is a continuous surface, and wherein the inner substrate is configured to resiliently deform in response to a force generated by the metamorphic material such that haptic feedback is translated to a region of the surface of the display.

13. The device of claim 11, wherein the actuator tab is an extension of the inner substrate.

14. The device of claim 11, wherein the actuator tab comprises a separate piece affixed to the body of the inner substrate.

15. The device of claim 11, wherein the actuator tab is configured such that, when the mutamorphic material generates a force, the force creates an in-plane displacement of the body of the inner substrate.

16. The device of claim 11, wherein the mutamorphic material comprises a polymer.

17. The device of claim 11, further comprising at least a portion of a display component integrated into the inner substrate.

18. The device of claim 17, further comprising at least a portion of a touch sensor integrated into the inner substrate.

19. The device of claim 11, further comprising:
a processor;
a memory, coupled to the processor, storing instructions configured to generate a haptic output with the haptic output device;
a haptic controller coupled to the processor and the haptic output device and configured to generate a signal configured to activate the haptic output device.

20. The device of claim 19, wherein the touch sensor comprises a first array of touch sensor conductors disposed on at least a portion of the inner substrate and joined to a second array of touch sensor conductors at least in part via an edge seal adhesive.

21. The device of claim 20, wherein the second array of touch sensor conductors are disposed on at least a portion of the display.

22. The device of claim 11, wherein the display and a first portion of the touch sensor are integrated into a first package, and wherein the haptic output device and a second portion of the touch sensor are integrated into a second package.

23. The device of claim 11, wherein a first surface of the touch sensor is attached to a surface of the display opposite the user facing surface, and the haptic output device is affixed to a second surface of the touch sensor that is opposite the first surface of the touch sensor.

24. The device of claim 11, wherein the actuator tab neck is a first actuator tab neck, and wherein the actuator tab further comprises a second actuator tab neck connected to the inner substrate.

25. A method comprising:
forming an actuator tab having an actuator tab neck connected to a bottom surface of a substrate on at least one side of the actuator tab such that one or more remaining sides of the actuator tab remain separated from the body of the substrate, the actuator tab being configured to translate haptic feedback to a region of a continuous surface of a display coupled to a top surface of the substrate;
affixing a mutamorphic material to at least a portion of the actuator tab;
applying an electrical connector to the mutamorphic material; and
affixing a haptic shield to the substrate, wherein the haptic shield is located between the display and the electrical connector.

26. The method of claim 25, wherein the actuator tab neck is connected to the body of the substrate with welding.

27. The method of claim 25, further comprising:
affixing the substrate as a component layer of a plurality of affixed component layers, the plurality of affixed component layers comprising a touch sensor.

28. The method of claim 25, wherein the one or more sides of the actuator tab that remain separated are formed by punching or etching.

29. A method comprising:
providing a haptic shield layer;
forming, on a first surface of the haptic shield layer, a copper trace layer comprising at least one conductive haptic actuator trace, the at least one haptic actuator trace being connected to a trace pad;
affixing a spacer layer to the copper trace layer, the spacer layer including an opening that causes the trace pad to be exposed;
affixing a mutamorphic material on the copper trace layer via the opening;
affixing a flex connector to the mutamorphic material, the flex connector coupling the mutamorphic material to the trace pad; and
coupling a display component to a second surface of the haptic shield layer.

30. The method of claim 29, wherein the haptic shield layer comprises a copper flood layer coupled to an electrical ground to provide for electrical shielding between a first component located on a first side of the haptic shield layer and a second component located on a second side of the haptic shield layer.

31. The method of claim 29, further comprising coupling the flex connector to a haptic controller to provide an electrical pathway from the haptic controller to the flex connector.

* * * * *